(12) United States Patent
Mullet et al.

(10) Patent No.: US 8,309,793 B2
(45) Date of Patent: Nov. 13, 2012

(54) DISCOVERY AND UTILIZATION OF SORGHUM GENES (MA5/MA6)

(75) Inventors: John E. Mullet, College Station, TX (US); William L. Rooney, College Station, TX (US); Patricia E. Klein, College Station, TX (US); Daryl Morishige, Bryan, TX (US); Rebecca Murphy, Bryan, TX (US); Jeff A. Brady, Stephenville, TX (US)

(73) Assignee: The Texas A&M University System, College Station, TX (US)

( * ) Notice: Subject to any disclaimer, the term of this patent is extended or adjusted under 35 U.S.C. 154(b) by 227 days.

(21) Appl. No.: 12/507,053

(22) Filed: Jul. 21, 2009

(65) Prior Publication Data

US 2010/0024065 A1    Jan. 28, 2010

Related U.S. Application Data

(60) Provisional application No. 61/082,388, filed on Jul. 21, 2008.

(51) Int. Cl.
*A01H 1/04* (2006.01)

(52) U.S. Cl. ..................................................... 800/267

(58) Field of Classification Search .................. None
See application file for complete search history.

(56) References Cited

U.S. PATENT DOCUMENTS

| | | | |
|---|---|---|---|
| 6,265,637 B1 | 7/2001 | Coupland et al. | 800/290 |
| 6,713,663 B2 | 3/2004 | Weigel et al. | 800/290 |
| 7,230,158 B2 | 6/2007 | Johanson et al. | 800/290 |
| 7,572,953 B2 | 8/2009 | Cheng et al. | 800/298 |
| 2002/0029395 A1 | 3/2002 | Weigel et al. | 800/290 |
| 2003/0093835 A1 | 5/2003 | Weigel et al. | 800/290 |
| 2006/0059586 A1 | 3/2006 | Cheng et al. | 800/298 |
| 2007/0050866 A1 | 3/2007 | Kiyosue et al. | 800/290 |
| 2008/0066198 A1 | 3/2008 | Nilsson et al. | 800/298 |

OTHER PUBLICATIONS

Rooney et al (1999, Crop Science 39:397-400).*
Crasta et al (1999, Mol. Gen. Genet. 262:579-588).*
Morgan et al., "Opportunities to improve adaptability and yield in grasses: lessons from sroghum," *Crop Sci.*, 42:1791-1799, 2002.
Childs et al., "The sorghum photoperiod sensitivity gene, Ma3, encodes a phytochrome B1," *Plant Physiol.*, 113:611-619, 1997.
Crasta et al., "Mapping of post-flowering drought resistance traits in grain sorghum: association between QTLs influencing premature senescence and maturity," *Mol. Gen. Genet.*, 262:579-588, 1999.
Craufurd et al., "Adaptation of sorghum: characterisation of genotypic flowering responses to temperature and photoperiod," *Theor. Appl. Genet.*, 99:900-911, 1999.
Feltus et al., "Alignment of genetic maps and QTLs between inter- and intraspecific sorghum populations," *Theor. Appl. Genet.*, 112:1295-1305, 2006.
Hart et al., "Genetic mapping of sorghum bicolor (L.) Moench QTLs that control variation in tillering and other morphological characters," *Theor. Appl. Genet.*, 103:1232-1242, 2002.
Klein et al., "The effect of tropical sorghum conversion and inbred development on genome diversity as revealed by high-resolution genotyping," *Plant Genome*, 48(Suppl.1):S12-S26, 2008.
Lee et al., "Photoperiod control of gibberellin levels and flowering of sorghum," *Plant Physiol.*, 116:1003-1011, 1998.
Lin et al., "Comparative analysis of QTLs affecting plant height and maturity across the poaceae, in reference to an interspecific sorghum population," *Genetics*, 141(1):391-411, 1995.
Miller et al., "Effect of tropical photoperiods on the growth of sorghum when grown in 12 monthly plantings," *Crop Sci.*, 8:499-509, 1968.
Paterson et al., "The weediness of wild plants: molecular analysis of genes influencing dispersal and persistence of johnsongrass, sorghum halepense (L.) Pers," *Proc. Natl. Acad. Sci. USA*, 92:6127-6131, 1995.
Quinby et al., "Fourth maturity gene locus in sorghum," *Crop Sci.*, 6(6):516-518, 1966.
Quinby et al., "Heterosis in sorghum resulting from the heterozygous condition of a single gene that affects duration of growth," *Amer. J. of Botany*, 33:716-721, 1946.
Quinby, "Genetics of Maturity," In: Sorghum improvement and the genetics of growth, pp. 18-29, Texas A& M Univeristy Press, College Station, Texas, 1974.
Rooney et al., "Genetic control of a photoperiod-sensitve response in shorghum bicolor (L.) Moench," *Crop Sci.*, 39:397-400, 1999.

* cited by examiner

*Primary Examiner* — Stuart F. Baum

(74) *Attorney, Agent, or Firm* — SNR Denton US LLP

(57) ABSTRACT

Methods and composition for the production of non-flowering or late flowering *sorghum* hybrid. For example, in certain aspects methods for use of molecular markers that constitute the Ma5/Ma6 pathway to modulate photoperiod sensitivity are described. The invention allows the production of plants having improved productivity and biomass generation.

2 Claims, 5 Drawing Sheets

FIG. 1A

Score = 4187 bits (2177), Expect = 0.0
Identities = 2185/2190 (99%), Gaps = 0/2190 (0%)
Strand=Plus/Minus

```
Query  1     TGTAGTCAGCAACTGGCCACCGTGGACGGGCCTTCCCTCAGAGATGCCACCAGGATGATG  60
             ||||||||||||||||||||||||||||||||||||||||||||||||||||||||||||
Sbjct  2190  TGTAGTCAGCAACTGGCCACCGTGGACGGGCCTTCCCTCAGAGATGCCACCAGGATGATG  2131

Query  61    CTTCGGAATAACAACAATAATCTGAGGAGCAATGGCCCATCAGATGGCTTGCTCAGCAGG  120
             ||||||||||||||||||||||||||||||||||||||||||||||||||||||||||||
Sbjct  2130  CTTCGGAATAACAACAATAATCTGAGGAGCAATGGCCCATCAGATGGCTTGCTCAGCAGG  2071

Query  121   CCAACCCCTGCAGTACTCCAGGATGATGACGATGGTGGTGATGATGATACGGAAAACCAG  180
             ||||||||||||||||||||||||||||||||||||||||||||||||||||||||||||
Sbjct  2070  CCAACCCCTGCAGTACTCCAGGATGATGACGATGGTGGTGATGATGATACGGAAAACCAG  2011

Query  181   CAGCAGGAGGCGGTCTACTGGGAGCGCTTCCTCCAGAAGAAGACCATCAACGTCTTGCTC  240
             ||||||||||||||||||||||||||||||||||||||||||||||||||||||||||||
Sbjct  2010  CAGCAGGAGGCGGTCTACTGGGAGCGCTTCCTCCAGAAGAAGACCATCAACGTCTTGCTC  1951

Query  241   GTGGAGAGTGACGACTGCACTAGGCGGGTCGTCAGTGCCCTTCTTCGTCACTGCATGTAC  300
             ||||||||||||||||||||||||||||||||||||||||||||||||||||||||||||
Sbjct  1950  GTGGAGAGTGACGACTGCACTAGGCGGGTCGTCAGTGCCCTTCTTCGTCACTGCATGTAC  1891

Query  301   CAAGTTATCTCTGCTGAAAATGGCCAGCAAGCATGGAATTATCTTGAAGATAAGCAGAAC  360
             ||||||||||||||||||||||||||||||||||||||||||||||||||||||||||||
Sbjct  1890  CAAGTTATCTCTGCTGAAAATGGCCAGCAAGCATGGAATTATCTTGAAGATAAGCAGAAC  1831

Query  361   AACATAGATATTGTTTTGATTGAGGTTTTTATGCCCGGTGTGTCTGGAATTTCTCTGCTG  420
             ||||||||||||||||||||||||||||||||||||||||||||||||||||||||||||
Sbjct  1830  AACATAGATATTGTTTTGATTGAGGTTTTTATGCCCGGTGTGTCTGGAATTTCTCTGCTG  1771

Query  421   AGTAGGATCATGAGCCACAATATTTGCAAGAATATTCCAGTGATTATGATGTCTTCGAAT  480
             ||||||||||||||||||||||||||||||||||||||||||||||||||||||||||||
Sbjct  1770  AGTAGGATCATGAGCCACAATATTTGCAAGAATATTCCAGTGATTATGATGTCTTCGAAT  1711

Query  481   GATGCTAGGAATACAGTCTTTAAATGTTTGTCGAAAGGTGCTGTTGACTTTTTAGTCAAT  540
             ||||||||||||||||||||||||||||||||||||||||||||||||||||||||||
Sbjct  1710  GATGCTAGGAATACAGTCTTTAAATGTTTGTCGAAAGGTGCTGTTGACTTTTTAGTCAAG  1651

Query  541   CCTATACGTAAGAATGAACTTAAGAATCTTTGGCAGCATGTATGGAGACGGTGTCACAGC  600
             ||||||||||||||||||||||||||||||||||||||||||||||||||||||||||||
Sbjct  1650  CCTATACGTAAGAATGAACTTAAGAATCTTTGGCAGCATGTATGGAGACGGTGTCACAGC  1591

Query  601   TCAAGTGGTAGTGGAAGTGAAAGTGGCATTCAGACGCAGAAGTGTGGCAAATCAAAAGGT  660
             ||||||||||||||||||||||||||||||||||||||||||||||||||||||||||||
Sbjct  1590  TCAAGTGGTAGTGGAAGTGAAAGTGGCATTCAGACGCAGAAGTGTGGCAAATCAAAAGGT  1531

Query  661   GGAAAAGAATCTGGTAATAATAGTGGTAGCAATGACAGTCACGACAACGAAGCAGACATG  720
             ||||||||||||||||||||||||||||||||||||||||||||||||||||||||||||
Sbjct  1530  GGAAAAGAATCTGGTAATAATAGTGGTAGCAATGACAGTCACGACAACGAAGCAGACATG  1471

Query  721   GGACTTAATGCAAGGGATGACAGTGATAATGGCAGTGGCACTCAAGCGCAGAGCTCATGG  780
             |||||||||||||||||||||||||||||||||||||||| |||||||||||||||||||
Sbjct  1470  GGACTTAATGCAAGGGATGACAGTGATAATGGCAGTGGCACTCAAGCGCAGAGCTCATGG  1411

Query  781   ACTAAGTGTGCTGTGGAGATGGACAGCCCACAGGCAATGTCTCTGGATCAGTTAGCCGAT  840
             ||||||||||||||||||||||||||||||||||||||||||||||||| ||||||||||
Sbjct  1410  ACTAAGTGTGCTGTGGAGATGGACAGCCCACAGGCAATGTCTCTGGATCACTTAGCCGAT  1351

Query  841   TCACCTGATAGCACTTGTGCGCAAGTAATCCACCCAAAGTCAGAGATATGTAGCAACAGA  900
             ||||||||||||||||||||||||||||||||||||||||||||||||||||||||||||
Sbjct  1350  TCACCTGATAGCACTTGTGCGCAAGTAATCCACCCAAAGTCAGAGATATGTAGCAACAGA  1291
```

FIG. 1B

```
Query  901   CGGCTACCAGACGACTTCAAGGAAAAGGACTTGGAGATAGGTGGCCCTGGAAATTTATAT  960
             ||||||||||||||||||||||||||||||||||||||||||||||||||||||||||||
Sbjct  1290  CGGCTACCAGACGACTTCAAGGAAAAGGACTTGGAGATAGGTGGCCCTGGAAATTTATAT  1231

Query  961   ATAGATCACCAATCTTCCCCAAATGAGAGGCCTATCAAAGCAACAGATGGACGTTGTGAG  1020
             ||||||||||||||||||||||||||||||||||||||||||||||||||||||||||||
Sbjct  1230  ATAGATCACCAATCTTCCCCAAATGAGAGGCCTATCAAAGCAACAGATGGACGTTGTGAG  1171

Query  1021  TACCCACCAAAAAACAATTCGAAGGAGTCAATGATGCAAAATCTAGAGGACCCAACTGTT  1080
             ||||||||||||||||||||||||||||||||||||||||||||||||||||||||||||
Sbjct  1170  TACCCACCAAAAAACAATTCGAAGGAGTCAATGATGCAAAATCTAGAGGACCCAACTGTT  1111

Query  1081  CGAGCTGCTGATCTAATTGGTTCAATGGCCAAAAACATGGATACCCAGGAGGCAGCGAGA  1140
             ||||||||||||||||||||||||||||||||||||||||||||||||||||||||||||
Sbjct  1110  CGAGCTGCTGATCTAATTGGTTCAATGGCCAAAAACATGGATACCCAGGAGGCAGCGAGA  1051

Query  1141  GCTGCAGATACCCCTAATCTCCCTTCCAAAGTGCCAGAAGGGAAAGATAAGAACAAGCAT  1200
             ||||||||||||||||||||||||||||||||||||||||||||||||||||||||||||
Sbjct  1050  GCTGCAGATACCCCTAATCTCCCTTCCAAAGTGCCAGAAGGGAAAGATAAGAACAAGCAT  991

Query  1201  GACAAAATTTTGCCATCACTTGAGTTGAGTTTGAAGAGGTCGAGATCATGTGGATATGGT  1260
             |||||||||||||||||||||||||||||||||||||||||||||||||||||| |||||
Sbjct  990   GACAAAATTTTGCCATCACTTGAGTTGAGTTTGAAGAGGTCGAGATCATGTGGAGATGGT  931

Query  1261  GCCAATACAGTCAAAGCTGATGAACAACAGAATGTATTAAGACAGTCAAATCTCTCAGCT  1320
             ||||||||||||||||||||||||||||||||||||||||||||||||||||||||||||
Sbjct  930   GCCAATACAGTCAAAGCTGATGAACAACAGAATGTATTAAGACAGTCAAATCTCTCAGCT  871

Query  1321  TTTACAAGGTACCATACATCTACGGCTTCCAATCAAGGTGGGACTGGATTAGTAGGGAGC  1380
             ||||||||||||||||||||||||||||||||||||||||||||||||||||||||||||
Sbjct  870   TTTACAAGGTACCATACATCTACGGCTTCCAATCAAGGTGGGACTGGATTAGTAGGGAGC  811

Query  1381  TGTTCGCCACATGACAACAGCTCAGAGGCTATGAAAACAGATTCTACTTACAACATGAAG  1440
             ||||||||||||||||||||||||||||||||||||||||||||||||||||||||||||
Sbjct  810   TGTTCGCCACATGACAACAGCTCAGAGGCTATGAAAACAGATTCTACTTACAACATGAAG  751

Query  1441  TCAAATTCAGATGCTGCTCCAATAAAACAAGGCTCCAACGGAAGTAGCAATAACAATGAC  1500
             ||||||||||||||||||||||||||||||||||||||||||||||||||||||||||||
Sbjct  750   TCAAATTCAGATGCTGCTCCAATAAAACAAGGCTCCAACGGAAGTAGCAATAACAATGAC  691

Query  1501  ATGGGTTCCACTACAAAGAATGTTGTGACAAAGCCCACTACAAATAATAAGGACAGGGTA  1560
             ||||||||||||||||||||||||||||||||||||||||||||||||||||||||||||
Sbjct  690   ATGGGTTCCACTACAAAGAATGTTGTGACAAAGCCCACTACAAATAATAAGGACAGGGTA  631

Query  1561  ATGTTGCCCTCATCAGCTATTAATAAGGCTAATGGACACACATCAGCATTCCACCCTGTG  1620
             ||||||||||||||||||||||||||||||||||||||||||||||||||||||||||||
Sbjct  630   ATGTTGCCCTCATCAGCTATTAATAAGGCTAATGGACACACATCAGCATTCCACCCTGTG  571

Query  1621  CAGCATTGGACGATGGTTCCAGCTAATGCAGCAGGAGGACAGCGAAGGCTGATGAAGTG  1680
             ||||||||||||||||||||||||||||||||||||||||||||||||||||||||||||
Sbjct  570   CAGCATTGGACGATGGTTCCAGCTAATGCAGCAGGAGGACAGCGAAGGCTGATGAAGTG  511

Query  1681  GCCAACATTGCAGGTTACCCTTCAGGTGACATGCAGTGTAACCTGATGCAATGGTACCCT  1740
             ||||||||||||||||||||||||||||||||||||||||||||||||||||||||||||
Sbjct  510   GCCAACATTGCAGGTTACCCTTCAGGTGACATGCAGTGTAACCTGATGCAATGGTACCCT  451

Query  1741  CGTCCAACCCTTCATTACGTCCAGTTTGATGGTGCACGGGAGAATGGTGGATCGGGAGCC  1800
             ||||||||||||||||||||||||||||||||||||||||||||||||||||||||||||
Sbjct  450   CGTCCAACCCTTCATTACGTCCAGTTTGATGGTGCACGGGAGAATGGTGGATCGGGAGCC  391

Query  1801  CTGGAATGTGGTTCCTCCAACGTATTTGATCCTCCAGTTGAAGGTCAAGCTACTAACTAT  1860
             ||| ||||||||||||||||||||||||||||||||||||||||||||||||||||||||
Sbjct  390   CTGCAATGTGGTTCCTCCAACGTATTTGATCCTCCAGTTGAAGGTCAAGCTACTAACTAT  331

Query  1861  GGTGTGAACAGGAGCAACTCAGGCAGTAACAATGCAACCAAGGGGCAGAATGGAAGTAAT  1920
             ||||||||||||||||||||||||||||||||||||||||||||||||||||||||||||
Sbjct  330   GGTGTGAACAGGAGCAACTCAGGCAGTAACAATGCAACCAAGGGGCAGAATGGAAGTAAT  271
```

FIG. 1C

```
Query  1921  ACAGTTGGTGCAAGCATGGCTGGTCCAAATGCAAATGCAAATGGTAATGCTGGACGAACA  1980
             ||||||||||||||||||||||||||||||||||||||||||||||||||||||||||||
Sbjct  270   ACAGTTGGTGCAAGCATGGCTGGTCCAAATGCAAATGCAAATGGTAATGCTGGACGAACA  211

Query  1981  AACATGGAGATTGCTAATGAGGTCATCGACAAAAGTGGACATGCAGGAGGTGGCAATGGG  2040
             ||||||||||||||||||||||||||||||||||||||||||||||||||||||||||||
Sbjct  210   AACATGGAGATTGCTAATGAGGTCATCGACAAAAGTGGACATGCAGGAGGTGGCAATGGG  151

Query  2041  AGTGGCAGTGGCAGTGGCAATGACACATATGTCAAACGGCTTGCAGCGGGCTTGACACCA  2100
             ||||||||||||||||||||||||||||||||||||||||||||||||||||||||||||
Sbjct  150   AGTGGCAGTGGCAGTGGCAATGACACATATGTCAAACGGCTTGCAGCGGGCTTGACACCA  91

Query  2101  CGACAAGCACAACTAAAGAAATATAGAGAGAAAAAGAAAGATCGAAACTTTGGGAAAAAG  2160
             ||||||||||||||||||||||||||||||||||||||||||||||||||||||||||||
Sbjct  90    CGACAAGCACAACTAAAGAAATATAGAGAGAAAAAGAAAGATCGAAACTTTGGGAAAAAG  31

Query  2161  GTAGCCTGTTTTCAATTGCATGTTTGTGGT  2190
             ||||||||||||||||||||||||||||||
Sbjct  30    GTAGCCTGTTTTCAATTGCATGTTTGTGGT  1
```

CSQQLATVDGPSLRDATRMMLRNNNNNLRSNGPSDGLLSRPTPAVLQDDDDGGDDDTENQQQEAVYWE
RFLQKKTINVLLVESDDCTRRVVSALLRHCMYQVISAENGQQAWNYLEDKQNNIDIVLIEVFMPGVSGISL
LSRIMSHNICKNIPVIMMSSNDARNTVFKCLSKGAVDFLVKPIRKNELKNLWQHVWRRCHSSSGSGSESGI
QTQKCGKSKGGKESGNNSGSNDSHDNEADMGLNARDDSDNGSGTQAQSSWTKCAVEMDSPQAMSLDHL
ADSPDSTCAQVIHPKSEICSNRRLPDDFKEKDLEIGGPGNLYIDHQSSPNERPIKATDGRCEYPPKNNSKESM
MQNLEDPTVRAADLIGSMAKNMDTQEAARAADTPNLPSKVPEGKDKNKHDKILPSLELSLKRSRSCGDGA
NTVKADEQQNVLRQSNLSAFTRYHTSTASNQGGTGLVGSCSPHDNSSEAMKTDSTYNMKSNSDAAPIKQG
SNGSSNNNDMGSTTKNVVTKPTTNNKDRVMLPSSAINKANGHTSAFHPVQHWTMVPANAAGGTAKADE
VANIAGYPSGDMQCNLMQWYPRPTLHYVQFDGARENGGSGALQCGSSNVFDPPVEGQATNYGVNRSNS
GSNNATKGQNGSNTVGASMAGPNANANGNAGRTNMEIANEVIDKSGHAGGGNGSGSGSGNDTYVKRLA
AGLTPRQAQLKKYREKKKDRNFGKKVA?FSIACLW 2.2

CSQQLATVDGPSLRDATRMMLRNNNNNLRSNGPSDGLLSRPTPAVLQDDDDGGDDDTENQQQEAVYWE
RFLQKKTINVLLVESDDCTRRVVSALLRHCMYQVISAENGQQAWNYLEDKQNNIDIVLIEVFMPGVSGISL
LSRIMSHNICKNIPVIMMSSNDARNTVFKCLSKGAVDFLVNPIRKNELKNLWQHVWRRCHSSSGSGSESGIQ
TQKCGKSKGGKESGNNSGSNDSHDNEADMGLNARDDSDNGSGTQAQSSWTKCAVEMDSPQAMSLDQLA
DSPDSTCAQVIHPKSEICSNRRLPDDFKEKDLEIGGPGNLYIDHQSSPNERPIKATDGRCEYPPKNNSKESMM
QNLEDPTVRAADLIGSMAKNMDTQEAARAADTPNLPSKVPEGKDKNKHDKILPSLELSLKRSRSCGYGAN
TVKADEQQNVLRQSNLSAFTRYHTSTASNQGGTGLVGSCSPHDNSSEAMKTDSTYNMKSNSDAAPIKQGS
NGSSNNNDMGSTTKNVVTKPTTNNKDRVMLPSSAINKANGHTSAFHPVQHWTMVPANAAGGTAKADEV
ANIAGYPSGDMQCNLMQWYPRPTLHYVQFDGARENGGSGALECGSSNVFDPPVEGQATNYGVNRSNSGS
NNATKGQNGSNTVGASMAGPNANANGNAGRTNMEIANEVIDKSGHAGGGNGSGSGSGNDTYVKRLAAG
LTPRQAQLKKYREKKKDRNFGKKVA?FSIACLW

FIG. 3

```
Query   39   AGCCGCCACGTACGTGCTTGCTTGCTAGCTGCTACAGAAGTGCTGGCGGTGGCGATGTAT   98
             ||||||||||||||||||||||||||||||||||||||||||||||||||||||||||||
Sbjct   53   AGCCGCCACGTACGTGCTTGCTTGCTAGCTGCTACAGAAGTGCTGGCGGTGGCGATGTAT   112

Query   99   ATATATGCCATAATGCCGAGCCAATTTCACCTCCTATTTTAGAGTATTTATTTATTTAAT   158
             |||||||||||||||||||||||||||||||||||||||||||| ||||||||||||| |
Sbjct   113  ATATATGCCATAATGCCGAGCCAATTTCACCTCCTATTTTAGAATATTTATTTATTTATT   172

Query   159  TACCTATTAT-----TGCCCAGGGAGCGAGTGTGGTTGGAAATT   197
             |||    ||||        ||||||  || ||||||||||||||||
Sbjct   173  TAC---TTATTATATTGCCCACGGAACGAGTGTGGTTGGAAATT   239

Query   198  AA-TTGGCTGCATCCCTACATTTTTACATTACTTGCACA--------------GGTACTGC   243
             || |||||||||||| |||||||||||||||| ||||||              ||||||||
Sbjct   240  AAATTGGCTGCATCC-TACATTTTTACATTACATGCACATACGGCACAGGCAGGTACTGC   298

Query   244  TGCCTAGTTAGCTATGAAACATGCATTGGCTTCATTATTCTGCTCTAACGGTACGAATGG   303
             |||||||||||||||||||||||||||||||||||||||||||||||||||||| |||||
Sbjct   299  TGCCTAGTTAGCTATGAAACATGCATTGGCTTCATTATTCTGCTCTAACGGTACAAATGG   358

Query   304  ATTCCTGGTTTCTTAAGGTTGCTTGCTCTTTTTGCCTTTTCGCAGGCCAGGCCACCACCA   363
             ||||||||||||||||| |||||||||||||||||||||||||||||||||| |||||||
Sbjct   359  ATTCCTGGTTTCTTAAGCTTGCTTGCTCTTTTTGCCTTTTCGCAGGCCAGGCAACCACCA   418

Query   364  ACCTCCACTTCCTCCATCCATCCATCCATTTGCTGCTGATTCACCACCTAGTAGCAGCAG   423
             ||||||||||||    ||||||||||||||||||||||||||||||||||         ||
Sbjct   419  ACCTCCACTTCC----TCCATCCATCCATTTGCTGCTGATTCACCACCT---------AG   465

Query   424  CAGCAGCTACACAGACACAGGTATTTTCTTCCCGGCCGGCCGGCGTCTCTCTACTCTCCT   483
             ||||||||||||||  ||||||||||||||||||||||||||||||||||||||||||||
Sbjct   466  CAGCAGCTACACAG--ACAGGTATTTTCTTCCCGGCCGGCCGGCGTCTCTCTACTCTCCT   523

Query   484  GCCTCCCATTCATTCTTCAGAGA--GCACGATTATTAATTTTCCAGAGGGCATGATTTAA   541
             |||||||||||||||||||||||  ||||  |||||||||||||||||||||||||||||
Sbjct   524  GCCTCCCATTCATTCTTCAGAGAGGGCACAATTATTAATTTTCCAGAGGGCATGATTTAA   583

Query   542  TGTCAATATCTCAAAATGATGCTACCCTCTTTCTCCCAGAGGGCCAGAGATATGATCCTT   601
             |||||||||||||||||||||||||||||||||||||||||||| |||||| ||||||||
Sbjct   584  TGTCAATATCTCAAAATGATGCTACCCTCTTTCTCCCAGAGGGACAGAGATTTGATCCTT   643

Query   602  TA    603 - 6bp - sequence with no match -
             ||
Sbjct   644  TA    645 - 33bp insertion with no match -

Query   609  TTGTTTTATCTTCCTACCTAGCTATATATAGCGATTCGTTTTGTCATTCACTTTGCAGCA   668
             ||||||||||||||||||||||||||||||||| ||||||||||||||||||||||||||
Sbjct   677  TTGTTTTATCTTCCTACCTAGCTATATATAGCTATTCGTTTTGTCATTCACTTTGCAGCA   736

Query   669  ATCACACAGACGAGGTGCCCTTGAAGGCGAACAAGGAGTAATATGCGCCCAGTGTCTAT   728
             |||||| ||||||||||||||||||||| |||||||||||||||||||||||||||||||
Sbjct   737  ATCACACTGACGAGGTGCCCTTGAAGGCAAACAAGGAGTAATATGCGCCCAGTGTCTAT   796

Query   729  TCACTAACCAACGACTTGCCTCGAATCAATCCCACCACTTTCGTCTACCTCTTCGAGTCA   788
             ||||||||||||||||||||||||||||||||||||||||||||||||||||||||||||
Sbjct   797  TCACTAACCAACGACTTGCCTCGAATCAATCCCACCACTTTCGTCTACCTCTTCGAGTCA   856

Query   789  GGCTGAGATATGCGAGGTGTCTGTAGTCAGCAACTGGCCA    828
             ||||||||||||||||||||||||||||||||||||||||
Sbjct   857  GGCTGAGATATGCGAGGTGTCTGTAGTCAGCAACTGGCCA    896
```

DISCOVERY AND UTILIZATION OF SORGHUM GENES (MA5/MA6)

This application claims priority to U.S. Provisional Application No. 61/082,388, filed on Jul. 21, 2008. The foregoing application is incorporated herein by reference in its entirety.

This invention was made with government support under grant number DBI-0321578 awarded by the U.S. National Science Foundation and grant number DE-FG02-06ER64306 awarded by the U.S. Department of Energy. The United States government has certain rights in the invention.

BACKGROUND OF THE INVENTION

1. Field of the Invention

The present invention relates generally to the field of plant genetics and molecular biology. More particularly, it concerns producing high biomass *sorghum* hybrids by utilizing molecular markers.

2. Description of Related Art

Biomass yield is one of the most important attributes of a biomass or bioenergy crop designed for ligno-cellulosic conversion to biofuels or bioenergy. Growth duration is a primary determinant of biomass yield, therefore late or non-flowering plants accumulate the most biomass assuming environmental conditions allow yield potential to be expressed.

Once grain *sorghum* initiates flowering, growth of the vegetative plant (stem, leaves) stops so that carbon and nitrogen compounds to be used for grain production. As a consequence, biomass accumulation overall decreases to some extent during the reproductive phase and ceases once grain filling has been completed (unless ratooning follows grain production).

In contrast, a late or non-flowering bioenergy *sorghum* crop grown for biomass production will continue to accumulate biomass by building larger vegetative plants until frost or adverse environmental conditions inhibit photosynthesis (e.g., drought, cold). It is estimated that late/non-flowering biomass *sorghum* will generate more than two times the biomass accumulated by grain *sorghum* per acre assuming reasonable growth conditions throughout the growing season. Therefore, there is a need for producing late or non-flowering *sorghum*.

SUMMARY OF THE INVENTION

The present invention overcomes a major deficiency in the art in producing high biomass *sorghum* hybrid by using molecular markers for selection.

In one aspect the invention provides a method for producing a late flowering or non-flowering hybrid *sorghum* plant comprising crossing a first early flowering *sorghum* plant with a second early flowering *sorghum* plant, wherein each of the first and second early flowering *sorghum* plants is homozygous recessive for at least one allele contributing to an early flowering phenotype, and wherein the first and second early flowering *sorghum* plants are not homozygous recessive for the same allele contributing to an early flowering phenotype. In one embodiment, the hybrid progeny plant comprises a dominant Ma7 or Ma3 allele.

In a further aspect, the invention provides crossing a first *sorghum* plant heterozygous dominant for at least a Ma5 or Ma6 allele with a second *sorghum* plant homozygous recessive for at least the Ma5 or Ma6 allele.

In yet a further aspect the invention provides crossing a first *sorghum* plant homozygous dominant for at least a Ma5 or Ma6 allele with a second *sorghum* plant homozygous recessive for at least the Ma5 or Ma6 allele.

In certain embodiments, the first or second early flowering *sorghum* plant may be produced by a) crossing a late flowering or non-flowering *sorghum* plant homozygous dominant for Ma5 and Ma6 comprising superior bioenergy properties with an early flowering *sorghum* plant homozygous recessive for a Ma5 or Ma6 allele; b) inbreeding a $F_1$ progeny; and c) selecting for an early flowering *sorghum* $F_2$ plant homozygous recessive for Ma5 or Ma6 but not homozygous recessive for the same Ma5 or Ma6 allele and comprising said superior bioenergy properties.

In another embodiment, the first or second early flowering *sorghum* plant may be produced by mutagenizing a late flowering or non-flowering *sorghum* plant to produce early flowering progeny comprising an inactive gene in a photoperiod sensing pathway. The gene in a photoperiod sensing pathway is selected from the group consisting of Ma3, Ma5, Ma6 and Ma7, in certain embodiments. For instance, the Ma3 gene may comprise a nucleic acid encoding PhyB, the Ma5 gene may comprise a nucleic acid encoding a COP9FUS5 homolog or a Myb-transcription factor, the Ma6 gene may comprise a nucleic acid encoding *sorghum* Prr37, and the Ma7 gene may comprise a nucleic acid encoding a polypeptide selected from the group consisting of PhyC, a MADS-box 14 protein and AP1.

In some embodiments, the first or second early flowering *sorghum* is selected from the group consisting of ATx623, EBA-3 and R.07007.

In certain embodiments the invention provides a method of selecting for a progeny plant of the cross according to the invention comprising marker-assisted selection comprising at least a first genetic marker genetically linked to a Ma5 or Ma6 allele. For instance, in one embodiment, the genetic marker genetically linked to the Ma5 allele may comprises a nucleic acid encoding a polypeptide selected from the group consisting of COP9FUS5 homolog and a Myb-transcription factor and in another embodiment, the genetic marker genetically liked to the Ma6 allele comprises a nucleic acid encoding a *sorghum* Prr37. The *sorghum* Prr37 polypeptide may comprises a lysine at position 166 or may be encoded by a nucleic acid molecule comprising SEQ ID NO:1, in particular embodiments of the invention.

In further embodiments, genetic markers in accordance with the invention may be linked to a quantitative trait locus (QTL). In some embodiments, the QTL is selected from the group consisting of FlrAvgB1, FlrAvgD1, FlrFstG1, FltQTL-DFG, FltQTL-DFB, QMa50.txs-A, QMa50.txs-C, QMa50.txs-F1, QMa50.txs-F2, QMa50.txs-H, QMa50.txs-I, QMa1.uga-G, QMa1.uga-D, and QMa5.uga-D.

In still further embodiments, genetic markers in accordance with the invention may be selected from the group consisting of sequence variants revealed by direct sequence analysis, restriction fragment length polymorphisms (RFLP), isozyme markers, allele specific hybridization (ASH), amplified variable sequences of plant genome, self-sustained sequence replication, simple sequence repeat (SSR) and arbitrary fragment length polymorphisms (AFLP).

Another aspect of the invention provides harvesting a progeny hybrid plant of the invention to produce biomass, bioenergy, bioproducts or sugar/starch. In yet another aspect, the invention provides a late flowering or non-flowering *sorghum* hybrid seed produced in accordance with the invention and *sorghum* hybrid plants grown from the seed.

In a further aspect, the invention provides a method of producing an inbred early flowering *sorghum* plant comprising: a) crossing a late flowering or non-flowering *sorghum* plant homozygous dominant for Ma5 and Ma6 with an early flowering sorghum plant homozygous recessive for a Ma5 or Ma6 allele; b) inbreeding the F₁ progeny; and c) selecting for an early flowering sorghum F₂ plant homozygous recessive for Ma5 or Ma6 but not homozygous recessive for the same Ma5 or Ma6 allele. In certain embodiments, the late flowering or non-flowering sorghum plant comprises superior bioenergy properties. In further embodiments, the selected early flowering sorghum F₂ plant comprises said superior bioenergy properties.

In yet a further aspect, the invention provides an inbreed early flowering sorghum seed produced in accordance with the invention and inbreed sorghum plants grown from the seed.

In certain aspects, the invention provides a method of identifying the genotype of a sorghum plant for a Ma5 or Ma6 allele comprising: a) obtaining a sorghum plant; and b) assaying the sorghum plant for a genetic marker genetically linked to the Ma5 or Ma6 allele. In one embodiment, the genetic marker genetically linked to the Ma5 allele may be a nucleic acid encoding a polypeptide selected from the group consisting of COP9FUS5 homolog and a Myb-transcription factor. In another embodiment, the genetic marker genetically linked to an Ma6 allele may be a nucleic acid encoding a sorghum Prr37 polypeptide. In certain embodiments, the sorghum Prr37 polypeptide may comprise a lysine at position 166 or may be encoded by a nucleic acid molecule comprising SEQ ID NO:1.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C: Alignment of EBA3 and RTx436 SbPRR37 cDNA sequences showing DNA sequence differences (bolded) (SEQ ID NOs:1 and 2).

FIG. 2: Comparison of protein sequences of Prr37 proteins encoded by EBA-3 and RTx436 derived from cDNA sequences. 2.1 corresponds to the sorghum Prr37 protein encoded by EBA-3 (Ma6) (SEQ ID NO:3) and 2.2 corresponds to the sorghum Prr37 protein encoded by RTx436 (ma6) (SEQ ID NO:4). An amino acid difference in the Prr37 protein putative dimerization domain is bolded and underlined; (K (lysine) in EBA-3, N (asparagine) in RTx436. Three additional differences in amino acid sequence are bolded.

FIG. 3: Alignment of partial promoter sequences of SbPRR37 derived from EBA-3 and RTx436. Query refers to EBA3 and Subject refers to BTx623 (SEQ ID NOs:6-9).

DESCRIPTION OF ILLUSTRATIVE EMBODIMENTS

I. The Present Invention

The instant invention overcomes several major problems with current sorghum production technologies in producing sorghum hybrids that have long duration of vegetative growth due to late flowering or lack of flowering, from inbreds that will flower sufficiently early in regions optimal for hybrid seed production, by manipulation of several QTL and the corresponding genes/alleles that constitute the Ma5/Ma6 pathway that regulates photoperiod sensitivity and flowering time in sorghum. Further embodiments and advantages of the invention are described below.

II. Sorghum

Increased demands on the agricultural and forestry industries due to world population growth, especially recent urgent need in biofuels production, have resulted in efforts to increase plant production and/or size. Sorghum has been an excellent biomass source with its high yield potential, high water use efficiency, and established production systems. Certain embodiments of the present invention disclose methods to generate sorghum genotypes with the genetic potential for improved biomass production.

Sorghum is a genus of numerous species of grasses, some of which are raised for grain and many of which are used as fodder plants either cultivated or as part of pasture. The plants are cultivated in warmer climates worldwide. Species are native to tropical and subtropical regions of all continents in addition to Oceania and Australasia. Sorghum is in the subfamily Panicoideae and the tribe Andropogoneae (the tribe of big bluestem and sugar cane). Sorghum is known as great millet and guinea corn in West Africa, kafir corn in South Africa, dura in Sudan, mtama in eastern Africa, jowar in India and kaoliang in China.

Sorghum is well adapted to growth in hot, arid or semi-arid areas. The many subspecies are divided into four groups—grain sorghums (such as milo), grass sorghums (for pasture and hay), sweet sorghums (formerly called "Guinea corn", used to produce sorghum syrups), and broom corn (for brooms and brushes). The name "sweet sorghum" is used to identify varieties of Sorghum bicolor that are sweet and juicy. High biomass Sorghum as a source of biofuels has also drawn a lot of attention recently.

Sorghum species contemplated in this invention include, but are not limited to, Sorghum almum, Sorghum amplum, Sorghum angustum, Sorghum arundinaceum, Sorghum bicolor (primary cultivated species), Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum timorense, Sorghum trichocladum, Sorghum versicolor, Sorghum virgatum, and Sorghum vulgare.

III. Photoperiod Sensitivity

The present invention relates to methods of modulating photoperiod sensitivity and flowering time in sorghum for high biomass production. Photoperiod sensitivity refers to the fact that some plants will not flower until they are exposed to day lengths that are less than a critical photoperiod (short day plants) or greater than a critical photoperiod (long day plants). Long day (LD) and short day (SD) plant designations refer to the day length required to induce flowering. Facultative LD or SD plants are those that show accelerated flowering in LD or SD but will eventually flower regardless of photoperiod. Most plants including sorghum must pass through a juvenile stage (lasting ~14-21 days for sorghum) before they become sensitive to photoperiod.

Sorghum is a facultative SD plant where long days inhibit flowering and short days accelerate flowering. The degree of photoperiod sensitivity in sorghum refers to the length of the short days that are required to induce flowering. A highly photoperiod sensitive sorghum will require photoperiods less than ~12 hours before flowering occurs whereas plants with low photoperiod sensitivity only require day lengths less than ~14 hours to induce flowering. Different sorghum genotypes vary in their degree of photoperiod sensitivity. Sorghum inbreds have been identified with photoperiod sensitivity ranging from ~10.5 to ~14 hours and still others that are nearly completely insensitive to photoperiod. For example, in College Station, Tex., photoperiod insensitive sorghum planted in April will flower in approximately 48-55 days. In contrast, highly photoperiod sensitive sorghum hybrids with the Ma5/Ma6 genotype flower in mid to late September in College Station, Tex. (~175-180 days).

For example, "early flowering sorghum" may be a plant that flowers in 50 to 120 days after planting between April 1 and April 19 in College Station, Tex.; a "late or non-flowering sorghum" may be a plant that flowers 150 to 200 or more days after planting or does not flower under these conditions The number of days to flowering will depend on the planting date and latitude where a sorghum genotype is planted because these factors determine when the plants are exposed to days that are sufficiently short to induce flowering. In general, late flowering photoperiod sensitive plants such as sorghum with the genotype Ma5_Ma6_ will not flower until day lengths are less than 12.2 hrs, whereas less photoperiod sensitive early flowering sorghum with recessive forms of Ma5, and Ma6 (and potentially Ma 7, Ma3, Ma1, etc.) will flower when exposed to day lengths (photoperiods) of ~12.4-14 hr or longer depending on genotype.

A. Utility of the Ma5/Ma6 System for Bioenergy Sorghum Hybrid Production

Certain aspects of this invention involve the use of the Ma5/Ma6 system to produce early flowering inbreds that when crossed generate high biomass or bioenergy sorghum hybrid seed that can be planted at any time of the year suitable for production, where the hybrid plants will have long growth duration (i.e., late flowering or non-flowering) at all latitudes from ~40 degrees N/S to the equator (40N=the upper midwest where sorghum growth is limited by cold). In another aspect, this same flowering control system can also be used to design sweet sorghum hybrids that grow for a specified number of days prior to flowering at different latitudes from early flowering inbreds suitable for hybrid seed production.

Table 1 below describes the relationship between latitude and daylength at planting and harvest for biomass/bioenergy production regions from ~40 degrees N/S to the equator. At higher latitudes, planting date is later in the year and harvesting occurs earlier due to longer duration of winter and low temperatures (shorter season). At lower latitudes, planting can be done earlier in the year or virtually any time in some locations and harvesting later in the year or multiple times during the year, including times of the year when daylength is less than 12 hours (Table 1).

TABLE 1

Relationship between latitude of crop production and daylength

| City | Latitude | Planting date | Daylength hours | Harvest date | Daylength hours |
|---|---|---|---|---|---|
| DesMoines, IA | 41.35 N | 15-May | 14.3 | 1-Oct | 11.6 |
| New York, NY | 40.42 N | 30-May | 14.6 | 1-Oct | 11.6 |
| Amarillo, TX | 35.05 N | 15-May | 13.8 | 15-Oct | 11.1 |
| College Station, TX | 30.37 N | 20-Mar | 11.7 | 15-Nov | 10.4 |
| Beaumont, TX | 30.05 N | 20-Mar | 11.8 | 15-Nov | 10.5 |
| Weslaco, TX | 26.09 N | 20-Mar | 11.8 | 1-Dec | 10.5 |
| Puerto Rico | 18.57 N | monthly | 10.8-13.2 | monthly | 10.8-13.2 |
| Panama City | 08.57 N | monthly | 11.4-12.6 | monthly | 11.4-12.6 |
| Equator | 0 | monthly | 12 | monthly | 12 |
| Brazilia, Brazil | 16.12 S | monthly | 11.1-12.9 | monthly | 11.1-12.9 |
| Brisbane, AU | 27.30 S | 20-Sep | 11.9 | 15-Mar | 12.2 |

Sorghum is insensitive to photoperiod during the juvenile phase which lasts for ~14-21 days post planting depending on genotype. Therefore, bioenergy sorghum hybrids need to have sufficient photoperiod sensitivity to prevent flowering at the daylengths that occur ~14-21 days post-planting at all latitudes used for bioenergy crop production. In addition, bioenergy sorghum hybrids that are planted in long days that block flowering may also require increased photoperiod sensitivity in order to block flowering prior to frost or harvest if daylengths decrease significantly during the growing season.

Certain aspects of the present invention involves the identification of allelic combinations of Ma5/Ma6 and other genes that repress flowering that work in hybrid combination to block flowering at daylengths as short as 11-10.5 hours. The early flowering inbreds used to produce late/non-flowering hybrid seed are designed to flower early due to different recessive genes that control flowering time. Therefore, when these inbreds are crossed, the F1 hybrids contain dominant genes at all loci involved thereby delaying flowering until plants are exposed to very short photoperiods.

Certain embodiments of the present invention provide sorghum genotypes that contain versions of Ma5 and Ma6 that in combination delay flowering until day lengths are less than 12 hr 20 min (Rooney and Aydin, 1999). There is evidence that additional genes such as Ma1-Ma4 enhance sorghum photoperiod sensitivity. In addition, it is likely that different alleles of Ma5 and Ma6 exist that can be used to make bioenergy sorghum hybrids even more photoperiod sensitive (less than 12 hr) increasing their utility for growing regions closer to the equator where bioenergy sorghum will be planted and grown in day lengths shorter than 12 hours (Table 1). For example, a study by Miller et al. (1968) identified five groups of *sorghum* that had short day requirements for flowering that ranged from ~13 hr to ~11.1 hr. This genetic material, and other genotypes identified in accordance with the present invention, flower late when growing at low latitudes in places such as Puerto Rico. In another study, Craufurd et al. (1999) identified *sorghum* genotypes with critical photoperiods between 10.2 and 11 hrs. In certain aspects of the invention, these materials have been investigated to identify genes with similar action to Ma5/Ma6 and alleles of Ma5 and Ma6 that would be useful for breeding PS hybrids for use over the entire range of latitudes from 40N/S to the equator.

B. Genetic Pathway of Photoperiod Sensitivity and Uses Thereof

Photoperiod sensitivity and late flowering is mediated in *sorghum* and rice by genes that repress activation of FT (flowering locus T) and AP1 and the transition of the apex from vegetative growth to forming reproductive structures. The repressors of flowering in *sorghum* act in a dominant fashion. The repressors are inactivated or less active under short photoperiods (and thermal periods). The vegetative or non-flowering state is maintained in part by light mediated signaling through PhyB and PhyC and possibly from other sources (PhyA, etc.) and partly by output from a circadian clock. The light signaling pathway involves a series of steps and genes, some of which may act directly to repress FT, and others of which act downstream from the circadian clock through modulation of homologs of GI, CO, and other genes that modulate repression of FT.

The repressing pathway can be inactivated by disrupting the function of any of the genes that are in the signaling pathway (PHYB, PHYC, or a gene between the photoreceptors and FT, and genes involved in clock function or input/output). The disruption of a gene in the flower repression pathway converts a photoperiod sensitive genotype into a less photoperiod sensitive genotype or photoperiod insensitive genotype that will flower early or at longer day lengths. If genotypes that are photoperiod insensitive due to inactivation of different genes in the flowering repression pathway are crossed, then the hybrid will be photoperiod sensitive and later flowering because active alleles contributed by the gametes from each line complement inactive alleles present in the gametes/genome of the other parental inbred line.

IV. Production of Photoperiod Sensitive Hybrid Using Ma5/Ma6 System

In certain aspects of the present invention, early flowering inbred *sorghum* genotypes with the proper allelic combinations of Ma5 and Ma6 can be crossed to produce photoperiod sensitive late-flowering *sorghum* hybrids (Ma5_Ma6_) ideal for biomass/bioenergy production with the use of molecular markers. In one embodiment, the early flowering photoperiod insensitive *sorghum* inbreds contain complementary pairs of dominant/recessive Ma5/Ma6 genes (Ma5ma6 and ma5Ma6 respectively).

One advantage of the Ma5/Ma6 system is the ability of this system to produce *sorghum* hybrids that have long duration of vegetative growth due to late flowering or lack of flowering, from inbreds that will flower sufficiently early in regions optimal for hybrid seed production (such as high plains of Texas).

The production of bioenergy *sorghum* hybrids is also important because hybrids are preferred commercially due to hybrid vigor that generates greater yield, and the ability to better control seed stocks through hybrid seed production.

The increase in yield attributed to hybrid vigor in *sorghum* is typically ~20% to ~50%. Photoperiod sensitive bioenergy *sorghum* hybrids that flower late or that do not flower are important for bioenergy production for several reasons: long duration of vegetative growth associated with late/non-flowering genotypes increases biomass yield per acre, high levels of photoperiod sensitivity will allow nearly year round planting of bioenergy *sorghum* hybrids at lower latitudes, and plants growing vegetatively (non-flowering) are more drought tolerant than plants that are in the reproductive phase of development; this is an important attribute of bioenergy *sorghum*.

A. Breeding Material and Methods

In further aspects of the present invention, naturally occurring alleles of Ma5 and Ma6 as well as other maturity genes (e.g., PHYB, PHYC) that are involved in the photoperiod-sensing pathway can be used to construct early flowering inbreds that can be crossed to produce late flowering hybrids.

In one embodiment, *sorghum* line R.07007 or EBA-3 is a primary source of both ma5 (recessive form) and Ma6 (dominant form), although other versions of Ma6 derived from photoperiod sensitive *sorghum* accessions may also be utilized. In another embodiment, dominant forms of Ma5 are derived from grain *sorghum* female lines that may be used for hybrid seed production.

In addition to working with naturally occurring genetic variants, certain embodiments of the present invention comprise mutagenizing any group of PS genotypes and identify PI lines derived from the parental lines that contain an inactive gene in the pathway that represses flowering. Crossing photoperiod insensitive early flowering genotypes that contain different inactive genes in the pathway that controls flowering time will generate photoperiod sensitive late flowering hybrids.

An exemplary approach involves screening photoperiod sensitive (late flowering) *sorghum* germplasm for accessions that express superior bioenergy traits. These accessions (most likely Ma5/Ma6) are then crossed to R.07007 or EBA-3 (ma5ma5ma7ma7Ma6Ma6). F2 progeny from these crosses that flower early (ma5ma5) but that retain Ma6Ma6 are selected by phenotyping and marker-assisted selection. The resulting early flowering inbreds (ma5ma5Ma6Ma6) can then be crossed with elite grain female A-lines that have the genotype (Ma5Ma5Ma7Ma7ma6ma6), to produce bioenergy hybrids that are Ma5_Ma7_Ma6_ that will flower late.

B. Sorghum Mutagenesis

In another aspect of the invention, mutagenesis of late flowering *sorghum* genotypes to create early flowering genotypes could be carried out in the following exemplary manner. The seed from a late flowering *sorghum* inbred would be germinated and treated with a mutagen such as EMS (ethyl methanesulphonate) or ENU (1-ethyl-1-nitrosourea) or using X-rays or neutron bombardment to induce changes in DNA sequence throughout the *sorghum* genomes of thousands of seedlings. The M1 seedlings (M1 refers to the first generation of plants that were exposed to a mutagen) surviving the treatment would be grown to maturity and self-pollinated. M2 seed derived from a large number of M1 plants would be grown out and screened for M2 plants that flower early under conditions where the parental inbred flowers late. An early flowering phenotype would be consistent with mutation in a gene that represses flowering such as Ma5 or Ma6.

C. Molecular Markers a. Marker Assisted Selection

Marker assisted selection or marker aided selection (MAS) is a process whereby a marker (morphological, biochemical or one based on DNA/RNA variation) is used for indirect selection of a genetic determinant or determinants of a trait of interest (e.g., productivity, disease resistance, abiotic stress tolerance, and/or quality). This process has been used in plant breeding.

Considerable developments in biotechnology have led plant breeders to develop DNA marker aided selection systems to augment traditional phenotypic-pedigree-based selection systems. Marker assisted selection (MAS) is an indirect selection process where a trait of interest is selected not based on the trait itself but on a marker linked to the gene (allele) that controls expression of the trait. For example if MAS is being used to select individuals with disease resistance, then a marker allele which is linked to the gene conferring disease resistance is scored or selected for rather than disease resistance per se. The assumption is that the marker allele is associated with the gene and/or quantitative trait locus (QTL) of interest that confers the trait under selection. MAS can be useful to select for traits that are difficult to measure, exhibit low heritability, and/or are expressed late in development.

In certain embodiments, a marker may be;

Morphological—First marker loci available that have obvious impact on morphology of plant. Genes that affect form, coloration, male sterility or resistance among others have been analyzed in many plant species. Examples of this type of marker may include the presence or absence of awn, leaf sheath coloration, height, grain color, aroma, etc.

Biochemical—A gene that encodes a protein that can be extracted and observed; for example, isozymes and storage proteins.

Cytological—The chromosomal banding produced by different stains; for example, G banding.

Biological—Different pathogen races or insect biotypes based on host pathogen or host parasite interaction can be used as a marker since the genetic constitution of an organism can affect its susceptibility to pathogens or parasites.

DNA-based and/or molecular—A unique (DNA sequence), occurring in proximity to or within the gene or locus of interest, can be identified by a range of molecular techniques such as direct sequencing, RFLPs, RAPDs, AFLP, DAF, SCARs, microsatellites, etc. DNA markers detect variation in DNA sequence, or DNA polymorphisms, that distinguish individuals. DNA polymorphisms include differences in single nucleotide sequences (SNPs), simple sequence repeats (SSRs), inversions or deletions (INDELS). DNA markers are designed to identify DNA sequence differences by one of several methods including; direct sequence analysis, electrophoretic separation of DNA fragment sizes following digestion of genomic DNA with restriction enzymes (RFLP) or after DNA amplification using PCR (AFLP, SSRs), or based on differences in amplification or probe hybridization (microarrays, Taqman probes, etc.).

As used herein, an "inherited genetic marker" is an allele at a single locus. A locus is a position on a chromosome, and allele refers to conditions of genes; that is, different nucleotide sequences, at those loci. The marker allelic composition of each locus can be either homozygous or heterozygous.

Coinheritance, or "genetic linkage," of a particular trait and a marker suggests that they are physically close together on the chromosome. Linkage is determined by analyzing the pattern of inheritance of a gene and a marker in a cross. The unit of recombination is the centimorgan (cM). Two markers are one centimorgan apart if they recombine in meiosis once in every 100 opportunities that they have to do so. The centimorgan is a genetic measure, not a physical one. Those markers located less then 50 cM from a second locus are said to be genetically linked, because they are not inherited independently of one another. Thus, the percent of recombination observed between the loci per generation will be less than 50%. In particular embodiments of the invention, markers may be used located less than about 45, 35, 25, 15, 10, 5, 4, 3, 2, or 1 or less cM apart on a chromosome.

The gene of interest is directly related with production of protein(s) or RNAs (e.g., miRNA) that produce certain phenotypes whereas markers should not influence the trait of interest but are genetically linked to an allelic form of a gene that modifies a trait (and so the marker and gene remain together during segregation of gametes due to the physical linkage between marker and gene, and a reduction in homologous recombination between the marker and gene of interest due to their close proximity on a strand of DNA). In many traits genes are discovered and can be directly assayed for their presence with a high level of confidence. However, if a gene is not isolated, marker's help is taken to tag a gene of interest. In such case there may be some false positive results due to recombination between marker of interest and gene (or QTL). A preferred marker that corresponds to or detects the difference in DNA sequence causing the desired phenotype or trait would elicit no false positive results.

In MAS, generally the first step is to map the gene or quantitative trait locus (QTL) of interest first by using one or more genetic mapping techniques and then use this information to identify DNA markers linked to and flanking the QTL useful for marker-assisted selection. Generally, the markers to be used should be close to the gene of interest (<5 recombination unit or cM) in order to ensure that only a minor fraction of the selected individuals will have a recombination between the DNA marker and target gene following any given cross or meiosis (specifically the DNA sequence variation within the target gene that causes the desired trait). Generally, not only a single marker but rather two markers are used that flank the target gene or QTL as closely as possible in order to reduce the chances of an error due to homologous recombination.

In plants QTL mapping is generally achieved using bi-parental cross populations involving two parents that have a contrasting phenotype for the trait of interest. Commonly used populations are recombinant inbred lines (RILs), doubled haploids (DH), back cross and F2. Linkage between the phenotype and markers that have already been mapped is tested in these populations in order to determine the position of the QTL on the overall genetic map. Such techniques are based on linkage and are therefore referred to as "linkage mapping".

In contrast to two-step QTL mapping and MAS, a single-step method for breeding typical plant populations has been developed (Rosyara et al., 2007). In such an approach, in the first few breeding cycles, markers linked to the trait of interest are identified by QTL mapping and later the same information in used in the same population. In this approach, pedigree structure is created from families that are created by crossing a number of parents (in three-way or four way crosses). Phenotyping is carried out and genotyping is done using molecular markers mapped the possible location of QTL of interest. This will identify markers and their favorable alleles. Once these favorable marker alleles are identified, the frequency of such alleles will be increased and response to marker-assisted selection is estimated. Marker allele(s) with desirable effect will be further used in next selection cycle or other experiments.

Recently high-throughput genotyping techniques are developed which allows marker aided screening of many genotypes. This will help breeders in shifting traditional breeding to marker-aided selection. One example of such automation is using DNA isolation robots and pipetting robots. A recent example of a high throughput DNA sequencer is the Illumina SGAII or ABI SOLID System.

Genetic markers and QTLs used in certain embodiments of the invention have been disclosed below.

In certain embodiments of the invention, molecular markers are developed that are polymorphic in parental lines of a cross or population, and linked to and flank the Ma5 and Ma6 QTL targeted for marker assisted selection (MAS). The molecular markers in some cases can correspond to and detect specific DNA sequence variants causing dominant or recessive gene action. In certain aspects, DNA may be extracted from the parental *sorghum* lines and progeny of a cross (F1, F2, backcross, testcross, RIL, etc.) and analyzed with molecular markers for the presence or absence of marker alleles linked to and flanking regions of the genome encoding dominant or recessive forms of Ma5 and/or Ma6. While any molecular marker assay technology could be used, biallelic (or multiallelic) marker assays such as SSRs, or assays such as direct sequencing that detect SNPs/indels are preferred.

b. Ma Genes

There are six classic maturity genes in *sorghum* that control flowering time termed Ma1-Ma6. Ma1, Ma2, Ma3 and Ma4 were identified by Quinby and his colleagues (Quinby and Karper, 1946; Quinby, 1966; Quinby, 1974). These loci/genes are part of a pathway that inhibits flowering. Therefore in general, *sorghum* plants with recessive Ma1-Ma6 genes (with low or no activity) flower earlier than plants with dominant or active Ma1-Ma6 genes that repress flowering. *Sorghum* plants that are Ma1Ma2Ma3Ma4 but recessive at either Ma5 or Ma6 will flower in ~74 days in College Station, Tex. when planted on April 19 (Rooney and Aydin, 1999) or in ~85 days when planted on June 1 in Plainview, Tex. (Quinby, 1974). Plants with recessive genes at Ma1-Ma4 (and recessive at Ma5 or Ma6) will flower in ~48-55 days post planting in these same locations. Ma5 and Ma6 are an additional pair of maturity loci that delay flowering when *sorghum* is planted ~April 19 in College Station, Tex. for ~175 days (mid-late September when photoperiods decrease below 12 h 20 min) (Rooney and Aydin, 1999). Based on information described in more detail below, it is predicted that late flowering Ma5/Ma6 plants also require an active PHYB gene (Ma3)

If an active form of PHYB (or Ma3) is required for Ma5/Ma6 genotypes to express photoperiod sensitivity and flower late, then complementary dominant/recessive forms of Ma3 could also be used to modulate differential flowering time in certain types of inbreds and hybrids. In this case, an early flowering inbred *sorghum* line that has the genotype ma3ma3Ma5Ma5Ma6Ma6 could be crossed to a second early flowering inbred *sorghum* genotype that has the genotype Ma3Ma3Ma5Ma5ma6ma6 in order to produce late flowering *sorghum* hybrids with the genotype Ma3ma3Ma5Ma5Ma6ma6.

Table 2 shows that information about the genetic map location of Ma1 and Ma3 has been published (Klein et al., 2008; Childs et al., 1997). Ma3 encodes the red light photoreceptor phytochrome B that is known to mediate repression of flowering in short day and long day plants (Childs et al., 1998). In addition, the inventors have collected information over the past several years on the genetic map locations of Ma5 and Ma7, loci required in combination with Ma6 to delay flowering ~175 days in College Station. Ma6 has also been mapped, as well as a modifier of Ma6 activity.

TABLE 2

*Sorghum* maturity (Ma) genes

| Locus | Map location | Gene | Reference |
| --- | --- | --- | --- |
| Ma1 | SBI06, ~11-21cM | Unknown | Klein et al., 2008 |
| Ma2 | Unknown | | |
| Ma3 | SBI01, ~166cM | PHYB | Childs et al., 1998 |
| Ma4 | Unknown | | |
| Ma5 | SBI02, ~145-148cM | | |
| Ma7 | SBI01, ~23-26cM | | |
| Ma6 | SBI06, ~11-19cM | | | b. *Sorghum* Flowering Time QTL

QTL (quantitative trait loci), quantitative trait inheritance or polygenic inheritance refers to the inheritance of a trait or phenotype that varies in degree of trait expression due to the interactions between two or more genes and the environment. QTL are genetic loci that span regions of a genome that encode genes that contribute to quantitative inheritance of a trait. The contributions of allelic forms of genes that contribute to quantitative traits and the genetic map locations of QTL can be characterized by analysis of populations derived by crossing parental lines that contain different allelic forms of genes that contribute to quantitative trait inheritance.

QTL mapping involves the genetic study of inheritance of alleles that occur in two or more loci and the phenotypes (physical forms or traits) that they produce. Because most traits of interest are governed by more than one gene, defining and studying the entire suite of genes and their alleles that modulate a trait provides an understanding of what effect the genotype of an individual has on the phenotype of that individual.

Genetic analysis involving statistical assessment is required to analyze the interaction of genes and to determine whether they produce a significant effect on the phenotype. QTL identify regions of the genome as containing allelic variation for one or more genes (or regulatory elements) that modulate the trait being assayed or measured. They are shown as intervals spanning a region of a chromosome, genetic map, or DNA sequence, where the probability of association is plotted for each marker used in the mapping experiment.

The QTL techniques were developed in the late 1980s and can be performed on populations of any species. To begin, a set of genetic markers must be developed for the species in question. A marker is an identifiable region of variable DNA sequence (single nucleotide or repeat variation, or inversions/deletions). Biologists are interested in understanding the genetic basis of phenotypes (i.e., physical traits). The aim is to find a marker that is significantly more likely to co-occur (co-segregate following a cross) with the trait than expected by chance, that is, a marker that has a statistically significant association with the trait. It is ideal to identify the specific gene or genes that modulate the trait in question, but this often requires a great deal of time and effort. Instead, they can more readily find regions of DNA that are very close to the genes in question. When a QTL is mapped, it identifies a region of the genome that spans the actual gene underlying the phenotypic trait although the region identified may also encode many genes that do not modulate the target trait.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes.

Another interest of statistical geneticists using QTL mapping is to determine the complexity of the genetic architecture underlying a phenotypic trait. For example, they may be interested in knowing whether a phenotype is modulated by many independent loci, or by a few loci, and do those loci interact. This can provide information on how expression of the phenotype is regulated.

Numerous QTL that modulate flowering time in *sorghum* have been identified in various studies (e.g., Lin et al., 1995, Paterson et al., 1995, Crasta et al., 1999, Hart et al., 2001; Feltus et al., 2006). The correspondence between QTL that modulate flowering time identified in genetic mapping studies and Ma1-Ma6 is not entirely clear because the location of Ma2 and Ma4 on the *sorghum* genetic map is not known. Information on various QTL for flowering time in *sorghum* is listed in Table 3.

TABLE 3

*Sorghum* flowering time QTL

Lin et al., 1995, Paterson et al., 1995; BTx623 × *S. propinquum*

| Locus | Map location | Marker |
|---|---|---|
| FlrAvgB1 | SBI02, ~102-119cM | UMC5, UMC139 |
| FlrAvgD1 | SBI06, ~9-21cM | |
| FlrFstG1 | SBI09, ~129-150cM | UMC132 |

Crasta et al., 1999; B35 × RTx430

| Locus | Map location | Gene |
|---|---|---|
| FltQTL-DFG | SBI10, ~70-74cM | UMC21 |
| FltQTL-DFB | SBI01, ~45cM | UMC27, ~10cM from PHYA |

Hart et al., 2001 (see map positions in Feltus et al., 2006 below) Feltus et al, 2006; summary of QTL from BTx623/IS3620C; BTx623/*S. propinquum*

| Locus | Map location | Marker |
|---|---|---|
| QMa50.txs-A | SBI01, ~182-186cM | Xgap36 |
| QMa50.txs-C | SBI03, ~140cM | Xumc16-Xtxs422 |
| QMa50.txs-F1 | SBI09, ~143cM | Xcdo393 |
| QMa50.txs-F2 | SBI09, ~143cM | Xcdo393 |
| QMa50.txs-H | SBI08, ~130-136cM | Xtxpl05-Xtxsl294 |
| QMaSO.txs-I | SBI06, ~10-36cM | Xumcll9-Xcdo718 |

Lin et al. (1995), Paterson et al. (1995)

| Locus | Map location | Marker |
|---|---|---|
| Qma1.uga-G | SBI09, ~129-150cM | Xumcl32-pSB445 |
| Qma1.uga-D | SBI06, ~31-59cM | data requires further analysis |
| QMa5.uga-D | SBI06, ~8-20cM | tiller flowering |

The relationship between Ma6 and Ma1 is uncertain at this time. The impact of Ma1 and Ma6 is quite different, but both QTL map to a similar region on SBI06 making it formally possible that Ma1 and Ma6 are different alleles of the same gene or different genes that reside in the same region of the genome.

Feltus et al. (2006) reported a flowering time QTL (QMa5.uga-D) that controls tiller flowering time that overlaps the region spanned by Ma1 and Ma6. It is formally possible that QMa5.ugaD corresponds to a different allele of Ma1 or Ma6 or a different flowering time gene.

Lin et al. (1995) mapped a flowering time QTL (FlrAvgD1=QMa1.ugaD) on SBI06 (31-59 cM) and suggested that this QTL could correspond to Ma1. Klein et al. (2008) using genotypes known to segregate for Ma1 showed that Ma1 mapped to an adjacent region on SBI06 (~11-21 cM). The data in Lin et al. (1995) are inconsistent with the assigned map location of QMa1.ugaD in Feltus et al. (2006). Data in Lin et al. (1995) show that QMa1.ugaD maps to the same location as QMa5.ugaD (Feltus et al., 2006).

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods for using Marker-Assisted Selection of *Sorghum* Inbreds that for Production of Photoperiod Sensitive Late or Non-Flowering *Sorghum* Hybrids In one non-limiting embodiment of the invention, molecular markers may be used to help convert a photoperiod sensitive (PS) late flowering inbred *sorghum* (A) that has the genotype Ma5Ma5Ma6Ma6 into a photoperiod insensitive (PI) early flowering inbred that can be used (crossed) in temperate regions to produce *sorghum* hybrid seed and hybrids that flower late. This can be done as follows:

a. Cross PS *sorghum* (A) with the genotype Ma5Ma5Ma6Ma6 to a PI *sorghum* (B) with the genotype ma5ma5Ma6Ma6 to generate an F1 plant.

b. Self the F1 plant and grow out F2 progeny.

c. Use DNA markers to identify progeny (C) that have the genotype ma5ma5Ma6Ma6.

d. The ma5ma5 alleles in (C) will be derived from (B).

e. The Ma6Ma6 alleles in (C) may be derived from either (A) or (B). Selection for the source of Ma6 allele may be important depending on the relative activity of the Ma6 alleles derived from (A) and (B).

f. Cross progeny with the genotype ma5ma5Ma6Ma6 (C) to an elite PI early flowering *sorghum* (D) with the genotype Ma5Ma5ma6ma6 to produce F1 seed.

g. F1 hybrid plants derived from this cross will be photoperiod sensitive and late or non-flowering with the genotype Ma5ma5Ma6ma6.

In another aspect, the method described above that starts with PS late flowering plants with the genotype Ma5Ma5Ma6Ma6 could involve several alternatives:

a. PI *sorghum* (B) used above could have the genotype ma5ma5ma6ma6.

In this case, progeny (C) identified by markers with the genotype ma5ma5Ma6Ma6 would have derived ma5 alleles from (B) and Ma6 alleles from (A).

b. PS *sorghum* (B) could have the genotype ma5ma5ma7ma7Ma6Ma6.

i. This is a case where recessive alleles in two different genes with Ma5-like action are needed to make progeny (C) PI, early flowering, and useful for the generation of PS *sorghum* hybrids.

ii. In this case, DNA markers would be used to identify progeny (C) that have the genotype ma5ma5ma7ma7Ma6Ma6.

iii. In this case, PI progeny (C) with the genotype ma5ma5ma7ma7Ma6Ma6 could be crossed to an elite PI line (D) with the genotype Ma5Ma5Ma7Ma7ma6ma6 to produce PS late or non-flowering *sorghum* hybrid seed/plants with the genotype Ma5ma5Ma7ma7Ma6ma6.

In a further aspects, inventors may want to convert a PI early flowering plant that is not suitable for use in the production of PS late or non-flowering *sorghum* hybrids into a PI early flowering plant that can be used for this purpose. This can be done as follows:

a. Cross a PI early flowering genotype (E) with the genotype ma5ma5ma6ma6 or Ma5Ma5ma6ma6 with a PI early flowering genotype (F) with the genotype ma5ma5Ma6Ma6.

b. Self the resulting F1 plants and use molecular markers to identify progeny (G) with the following genotype; ma5ma5Ma6Ma6.

c. The ma5ma5 alleles could be derived from (E) or (F) depending on the cross involved, whereas the Ma6Ma6 alleles will be derived from (F).

d. Cross progeny (G) to an elite *sorghum* with the genotype Ma5Ma5ma6ma6 to generate F1 seed/hybrid plants that are PS late or non-flowering.

Example 2

Genetic Map Analysis of Ma5

The location of Ma5, Ma7 and Ma6 on the *sorghum* genetic map was determined as described below thus enabling the development of DNA markers flanking these loci for use in marker-assisted breeding. The coordinates of Ma5, Ma7 and Ma6 on the TAMU *sorghum* genetic map (cM) and on the DOE *sorghum* genome sequence (bp) are listed below: (i) Ma5 QTL coordinates on SBI-02: From 59L10, 67923811 bp, 146.1-148.9 cM to txp428, 68393290 bp, 148.9-152.1 cM; (ii) Ma7 QTL coordinates on SBI-01: From txp208, 6545866 bp, 23.4 cM to txp523, 8017655 bp, 26.5-29.5 cM.

Populations segregating for Ma5/ma5 were constructed by crossing EBA-3 (ma5ma5Ma6Ma6) to A3RTx436 (Ma5Ma5ma6ma6) creating an F1 hybrid that was backcrossed to EBA-3 to create a BC1F1 mapping population that was expected to segregate 1:1 for alleles at the Ma5 locus (Ma5ma5Ma6_; ma5ma5Ma6_). Phenotypic analysis of flowering time of BC1F1 progeny was performed from this cross.

A large population of ~4200 BC1F1 plants was grown at two locations in College Station, Tex. and was assayed for days to flowering at approximately weekly intervals. The parents of this population flowered between 60-90 days, and the F1 flowered at ~170-180 days. Data on time to flowering was collected from 2915 plants, whereas the remaining plants either died during growth (a small number of plants) or had not flowered by November when frost terminated their development. Approximately 28% of the population flowered early (before August 7) and there was a period from 105-148 days post planting where fewer plants flowered before a second large cohort of plants initiated flowering. Approximately 72% of the plants flowered after August 7, with many plants flowering well after F1 hybrids flowered at approximately 175 days (more than 220 days). This result indicated that more than one gene with Ma5-like action was segregating in this population based on deviation from 1:1 segregation of PI:PS phenotypes and transgressive segregation for late flowering.

A form of bulk segregant analysis and SSR and AFLP markers were used to map the location of one locus with Ma5 action to a ~10 cM region on LG-02. This locus was designated Ma5. The location of Ma5 was further refined to a region ~250,000 bp. Information on the segregation of Ma5 and flowering phenotypes was used to map a second locus with Ma5 like action to LG-01. This locus was designated Ma7. The gene for Ma7 was further fine mapped to a region spanning ~400,000 bp. Portions of the *sorghum* genome sequence released by DOE to each of these regions and identified putative genes encoded by these regions based on BLAST analysis and comparison to the colinear region of the rice genome were identified and aligned.

The Ma5 and Ma7 loci were examined and candidate genes in these regions were identified that could explain the observed regulation of flowering time. In the Ma5 locus, a gene homologous to COP9FUS5 was identified as a candidate gene. COP9FUS5 is a subunit of a large signalasome complex (CSN complex) that was initially identified in *Arabidopsis* as involved in the repression of photomorphogenesis and a range of other activities. This complex acts by targeting transcription factors for degradation that mediate light activated events (such as de-etiolation, light activated gene expression). Therefore, it was reasoned that variation in the activity of COP9FUS5 could modulate flowering time in *sorghum* by modulating light dependent repression of flowering mediated by the PhyB and PhyC photoreceptors, or by modulating light dependent output from the circadian clock. A gene encoding a Myb-transcription factor that could be involved in flowering time was also identified in the Ma5 fine mapping interval. Myb-transcription factors such as CCA1/LHY (*Arabidopsis*) are a central part of the circadian clock and allelic variation in this type of gene can modulate flowering time.

Several candidate genes were identified in the Ma7 locus including PhyC, a MADS-box 14 gene and a MADS-box gene corresponding to AP1. AP1 activates meristem identity genes that are involved in the production of floral organs. AP1 is activated by FT in the apex. FT encodes a transmissible protein that travels from the leaf to the apex when photoperiod and other requirements are met such that FT expression is activated. MADS-box 14 is involved in flowering time control in rice so it is also a candidate gene for Ma7. PhyC is also a reasonable candidate for Ma7 because in rice, and presumably *sorghum*, inactivation of PhyC decreases repression of flowering in long days resulting in early flowering (as observed in EBA-3).

Example 3

Genetic Map Location and Molecular Description of Ma6

Ma6 was mapped in a BC1F1 population created by crossing EBA-3 (ma5ma5Ma6Ma6) to ATx623 (Ma5Ma5ma6ma6), where the F1 derived from this cross was backcrossed to ATx623. Progeny from the BC1F1 population were expected to segregate for the Ma6 locus in a 1:1 ratio (Ma5_ma6ma6 vs. Ma5_Ma6ma6). Late flowering plants from this population were expected to contain the EBA-3 dominant version of Ma6. Genetic mapping initially located Ma6 to an interval on SBI06 spanning from ~8 cM to ~21 cM (Ma6 QTL coordinates on LG-06: txp658, 39379760 bp, 8.0-9.9 cM to txp434, 42610705 bp, 17.4-20.7 cM; bp coordinates are derived from the DOE pseudomolecule sequence). Further fine mapping narrowed the Ma6 locus to a region spanning from Xtxp598 to a DNA polymorphism present in a DNA binding protein upstream from Ma6. There are approximately ~20 annotated genes (excluding genes associated with transposons) in this delimited region.

A *sorghum* gene encoding a homolog of *Arabidopsis* PRR7 (and rice OsPRR37) was present among the ~20 genes in the delimited Ma6 locus. The PRR7/PRR37 gene homologs are known to modulate flowering time in several plant species (*Arabidopsis*, rice, barley) suggesting that the *sorghum* PRR7/37 gene homolog in the Ma6 locus is likely to be the gene causing differences in flowering time in *sorghum*. Therefore, cDNA derived from this gene was sequenced from EBA-3 (Ma6) and RTx436 (ma6) and compared (FIGS. 1A-C; SEQ ID NOs: 1 and 2). The alignment of the cDNA sequences revealed 5 sequence polymorphisms (FIGS. 1A-C). One of these sequence differences (a G (EBA3) to T (RTx436) substitution) caused amino acid 166 to change from a lysine (EBA3) to an asparagine in RTx436 (FIG. 2). This amino acid change is conservative (no charge change) but occurs in a three amino acid sequence of the Prr protein predicted to be involved in dimerization. Therefore it is possible that this change in amino acid sequence alters protein-protein interaction required for normal function of the SbPrr37 protein.

The protein encoded by *sorghum* PRR37 (Ma6) is homologous to and similar in amino acid sequence to the protein encoded by rice PRR37. The rice Prr37 protein sequence is shown below, where the putative signal receiver domain is shown in bold and the putative dimerization domain (amino acids 166-168) is shown in bold and underlined (amino acid sequence KPI (lysine-proline-isoleucine). The *sorghum* Prr37 putative dimerization domain of EBA-3 (Ma6) has the sequence KPI (SEQ ID NO:3) identical to rice Prr37 (SEQ ID NO:5) (KPI at positions 166-168), whereas the putative dimerization domain of Prr37 from RTx436 (ma6) (SEQ ID NO:4) has the sequence NPI.

| Rice Prr7 protein features: Location/Qualifiers | |
|---|---|
| | recently identified in eukaroytes ETR1 *Arabidopsis thaliana*; this domain receives the signal from the sensor partner in a two-component systems; contains; cd00156" /db_xref="CDD:29071" |
| Site | order(68 . . . 69, 114, 122, 144, 163, 166 . . . 167) /site_type="active" /db_xref="CDD:29071" |
| Site | 114 /site_type="phosphorylation" /db_xref="CDD:29071" |
| Site | order(117 . . . 118, 120 . . . 122) /site_type="other" /note="intermolecular recognition site" /db_xref="CDD:29071" |
| Site | 166 . . . 168 /site_type="other" /note="dimerization interface" /db_xref="CDD:29071" |
| Region | 682 . . . 718 /region_name="CCT" /note="CCT motif. This short motif is found in a number of plant proteins. It is rich in basic amino acids and has been called a CCT motif after Co, Col and Toc1; pfam06203" /db_xref="CDD:87043" |
| CDS | 1 . . . 742 /gene="OsPRR37" /coded_by="AB189039.1:1 . . . 2229" |

A difference in the expression (gene regulation) of PRR37 in EBA-3 and RTx436 could cause a difference in gene activity corresponding to Ma6 vs. ma6. Preliminary assays showed

```
Rice Prr7 Sequence:
  1 mmgtahhnqt agsalgvgvg dandavpgag gggysdpdgg pisgvqrppq vcwerfiqkk 61 tikvllvdsd dstrqvvsal lrhcmyevip aengqqawty ledmqnsidl vltevvmpgv 121 sgisllsrim nhnicknipv immssndamg tvfkclskga vdflvkpirk nelknlwqhv 181 wrrchsssgs gsesgiqtqk caksksgdes nnnngsnddd dddgvimgln ardgsdngsg 241 tqaqsswtkr aveidspqam spdqladppd stcaqvihlk sdicsnrwlp ctsnknskkq 301 ketnddfkgk dleigsprnl ntayqsspne rsikptdrrn eyplqnnske aamenleess 361 vraadligsm aknmdaqqaa raanapncss kvpegkdknr dnimpslels lkrsrstgdg 421 anaiqeeqrn vlrrsdlsaf tryhtpvasn qggtgfmgsc slhdnsseam ktdsaynmks 481 nsdaapikqg sngssnnndm gsttknvvtk pstnkervms psavkanght safhpaqhwt 541 spanttgkek tdevannaak raqpgevqsn lvqhprpilh yvhfdvsren ggsgapqcgs 601 snvfdppveg haanygvngs nsgsnngsng qngsttavda erpnmeiang tinksgpggg 661 ngsgsgsgnd mylkrftqre hrvaavikfr qkrkernfgk kvryqsrkrl aeqrprvrgq 721 fvrqavqdqq qqgggreaaa dr
```

| Rice Prr7 protein features: Location/Qualifiers | |
|---|---|
| source | 1 . . . 742 /organism="*Oryza sativa Japonica* Group" /cultivar="Nipponbare" /db_xref="taxon:39947" |
| Protein | 1 . . . 742 /product="pseudo-response regulator 37" |
| Region | 65 . . . 180 /region_name="REC" /note="Signal receiver domain; originally thought to be unique to bacteria (CheY, OmpR, NtrC, and PhoB), now | that PRR37 was expressed differently in EBA-3 and RTx436. Therefore, ~800 bp of the promoter regions of PRR37 from EBA-3 and RTx436 was sequenced and aligned (FIG. 3). This revealed many sequence differences including several large deletions/insertions in the promoter regions of PRR37 in RTx436 compared to EBA-3 (FIG. 3). These differences in sequence may alter the expression of the PRR37 alleles and contribute to a difference in flowering phenotype.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Childs et al., *Plant Physiol.*, 116(3):1003-1011, 1998.
Childs et al., *Plant Physiol.*, 113:611-619, 1997.
Crasta et al., *Mol. Gen. Genet.*, 262(3):579-588, 1999.
Craufurd et al., *Theor. Appl. Genet.*, 99:900-911, 1999.
Feltus et al., *Theor. Appl. Genet.*, 112(7):1295-1305, 2006.
Hart et al., *Theor. Appl. Genet.*, 103: 1222-1242, 2001
Ishikawa et al., *Plant Cell*, 17(12):3326-3336, 2005.
Kaczorowski and Quail, *Plant Cell*, 15(11):2654-2665, 2003.
Klein et al., *Plant Genome*, 48: S12-22, 2008
Lin et al., *Genetics*, 141(1):391-411, 1995.
McClung, *Proc. Natl. Acad. Sci. USA*, 103(32):11819-11820, 2006.
Miller et al., *Crop Science*, 8:499-502, 1968.
Nakamichi et al., *Plant Cell Physiol.*, 48(6):822-832, 2007.
Paterson et al., *Proc. Natl. Acad. Sci. USA*, 92(13):6127-6131, 1995.
Quinby and Karper, *Amer. J. Botany*, 33(9):716-721, 1946.
Quinby, J. R., *Crop Science* 6:516-518, 1966
Quinby, J. R. (1974) *Sorghum Improvement and the Genetics of Growth*. Texas A&M University Press.
Rooney and Aydin, *Crop Science*, 39; 397-400, 1999.
Rosyara et al., In: *Family-based mapping of FHB resistance QTLs in hexaploid wheat*, Proc. Natl. Fusarium Head Blight Forum, Kansas City, Mo., 2007.
Takano et al., *Plant Cell*, 17(12):3311-3325, 2005.
Turner et al., *Science*, 310(5750):1031-1034, 2005.

What is claimed is:

1. A method of screening a sorghum plant for a Ma5 allele comprising:
   a) obtaining a sorghum plant; and
   b) assaying the sorghum plant for a genetic marker genetically linked to the Ma5 allele, wherein said Ma5 allele is located on chromosome 2 between coordinates 67923811 to 68393290 bp.

2. The method of claim 1, wherein the genetic marker is selected from the group consisting of sequence variants revealed by direct sequence analysis, restriction fragment length polymorphisms (RFLP), isozyme markers, allele specific hybridization (ASH), amplified variable sequences of plant genome, self-sustained sequence replication, simple sequence repeat (SSR) and arbitrary fragment length polymorphisms (AFLP).

* * * * *

SEQUENCE LISTING

<160> NUMBER OF SEQ ID NOS: 9

<210> SEQ ID NO 1
<211> LENGTH: 2190
<212> TYPE: DNA
<213> ORGANISM: Sorghum bicolor

<400> SEQUENCE: 1

```
tgtagtcagc aactggccac cgtggacggg ccttccctca gagatgccac caggatgatg      60
cttcggaata acaacaataa tctgaggagc aatggcccat cagatggctt gctcagcagg     120 ccaaccctg cagtactcca ggatgatgac gatggtggtg atgatgatac ggaaaaccag      180
cagcaggagg cggtctactg ggagcgcttc ctccagaaga agaccatcaa cgtcttgctc     240
gtggagagtg acgactgcac taggcgggtc gtcagtgccc ttcttcgtca ctgcatgtac     300
caagttatct ctgctgaaaa tggccagcaa gcatggaatt atcttgaaga taagcagaac     360
aacatagata ttgtttttgat tgaggttttt atgcccggtg tgtctggaat ttctctgctg     420
agtaggatca tgagccacaa tatttgcaag aatattccag tgattatgat gtcttcgaat     480
gatgctagga atacagtctt taaatgtttg tcgaaaggtg ctgttgactt tttagtcaag     540
cctatacgta agaatgaact taagaatctt tggcagcatg tatggagacg gtgtcacagc     600
tcaagtggta gtggaagtga aagtggcatt cagacgcaga agtgtggcaa atcaaaaggt     660
ggaaaagaat ctggtaataa tagtggtagc aatgacagtc acgacaacga agcagacatg     720
ggacttaatg caagggatga cagtgataat ggcagtggca ctcaagcgca gagctcatgg     780
actaagtgtg ctgtggagat ggacagccca caggcaatgt ctctggatca cttagccgat     840
tcacctgata gcacttgtgc gcaagtaatc cacccaaagt cagagatatg tagcaacaga     900
cggctaccag acgacttcaa ggaaaaggac ttggagatag gtggccctgg aaatttatat     960
atagatcacc aatcttcccc aaatgagagg cctatcaaag caacagatgg acgttgtgag    1020
tacccaccaa aaaacaattc gaaggagtca atgatgcaaa atctagagga cccaactgtt    1080
cgagctgctg atctaattgg ttcaatggcc aaaaacatgg atacccagga ggcagcgaga    1140
gctgcagata cccctaatct cccttccaaa gtgccagaag ggaaagataa gaacaagcat    1200
```

```
gacaaaattt tgccatcact tgagttgagt ttgaagaggt cgagatcatg tggagatggt    1260
gccaatacag tcaaagctga tgaacaacag aatgtattaa gacagtcaaa tctctcagct    1320
tttacaaggt accatacatc tacggcttcc aatcaaggtg ggactggatt agtagggagc    1380
tgttcgccac atgacaacag ctcagaggct atgaaaacag attctactta caacatgaag    1440
tcaaattcag atgctgctcc aataaaacaa ggctccaacg gaagtagcaa taacaatgac    1500
atgggttcca ctacaaagaa tgttgtgaca agcccactaa caaataataa ggacagggta    1560
atgttgccct catcagctat taataaggct aatggacaca catcagcatt ccaccctgtg    1620
cagcattgga cgatggttcc agctaatgca gcaggaggga cagcgaaggc tgatgaagtg    1680
gccaacattg caggttaccc ttcaggtgac atgcagtgta acctgatgca atggtaccct    1740
cgtccaaccc ttcattacgt ccagtttgat ggtgcacggg agaatggtgg atcgggagcc    1800
ctgcaatgtg gttcctccaa cgtatttgat cctccagttg aaggtcaagc tactaactat    1860
ggtgtgaaca ggagcaactc aggcagtaac aatgcaacca aggggcagaa tggaagtaat    1920
acagttggtg caagcatggc tggtccaaat gcaaatgcaa atggtaatgc tggacgaaca    1980
aacatggaga ttgctaatga ggtcatcgac aaaagtggac atgcaggagg tgcaatggg    2040 agtggcagtg gcagtggcaa tgacacatat gtcaaacggc ttgcagcggg cttgacacca    2100
cgacaagcac aactaaagaa atatagagag aaaaagaaag atcgaaactt tgggaaaaag    2160
gtagcctgtt ttcaattgca tgtttgtggt                                     2190

<210> SEQ ID NO 2
<211> LENGTH: 2190
<212> TYPE: DNA
<213> ORGANISM: Sorghum bicolor

<400> SEQUENCE: 2
tgtagtcagc aactggccac cgtggacggg ccttccctca gagatgccac caggatgatg      60
cttcggaata acaacaataa tctgaggagc aatggcccat cagatggctt gctcagcagg     120 ccaaccctg cagtactcca ggatgatgac gatggtggtg atgatgatac ggaaaaccag     180
cagcaggagg cggtctactg ggagcgcttc ctccagaaga agaccatcaa cgtcttgctc     240
gtggagagtg acgactgcac taggcgggtc gtcagtgccc ttcttcgtca ctgcatgtac     300
caagttatct ctgctgaaaa tggccagcaa gcatggaatt atcttgaaga taagcagaac     360
aacatagata ttgttttgat tgaggttttt atgcccggtg tgtctggaat ttctctgctg     420
agtaggatca tgagccacaa tatttgcaag aatattccag tgattatgat gtcttcgaat     480
gatgctagga atacagtctt taaatgtttg tcgaaaggtg ctgttgactt tttagtcaat     540
cctatacgta agaatgaact taagaatctt tggcagcatg tatggagacg tgtcacagc     600 tcaagtggta gtggaagtga aagtggcatt cagacgcaga agtgtggcaa atcaaaaggt     660
ggaaaagaat ctggtaataa tagtggtagc aatgacagtc acgacaacga agcagacatg     720
ggacttaatg caagggatga cagtgataat ggcagtggca ctcaagcgca gagctcatgg     780
actaagtgtg ctgtggagat ggacagccca caggcaatgt ctctggatca gttagccgat     840
tcacctgata gcacttgtgc gcaagtaatc cacccaaagt cagagatatg tagcaacaga     900
cggctaccag acgacttcaa ggaaaaggac ttggagatag gtggccctgg aaatttatat     960
atagatcacc aatcttcccc aaatgagagg cctatcaaag caacagatgg acgttgtgag    1020
tacccaccaa aaaacaattc gaaggagtca atgatgcaaa atctagagga cccaactgtt    1080
cgagctgctg atctaattgg ttcaatggcc aaaaacatgg atacccagga ggcagcgaga    1140
```

-continued

```
gctgcagata cccctaatct cccttccaaa gtgccagaag ggaaagataa gaacaagcat    1200
gacaaaattt tgccatcact tgagttgagt ttgaagaggt cgagatcatg tggatatggt    1260
gccaatacag tcaaagctga tgaacaacag aatgtattaa gacagtcaaa tctctcagct    1320
tttacaaggt accatacatc tacggcttcc aatcaaggtg ggactggatt agtagggagc    1380
tgttcgccac atgacaacag ctcagaggct atgaaaacag attctactta caacatgaag    1440
tcaaattcag atgctgctcc aataaaacaa ggctccaacg gaagtagcaa taacaatgac    1500
atgggttcca ctacaaagaa tgttgtgaca agcccactaa caaataataa ggacagggta    1560
atgttgccct catcagctat taataaggct aatggacaca catcagcatt ccaccctgtg    1620
cagcattgga cgatggttcc agctaatgca gcaggaggga cagcgaaggc tgatgaagtg    1680
gccaacattg caggttaccc ttcaggtgac atgcagtgta acctgatgca atggtaccct    1740
cgtccaaccc ttcattacgt ccagtttgat ggtgcacggg agaatggtgg atcgggagcc    1800
ctggaatgtg gttcctccaa cgtatttgat cctccagttg aaggtcaagc tactaactat    1860
ggtgtgaaca ggagcaactc aggcagtaac aatgcaacca aggggcagaa tggaagtaat    1920
acagttggtg caagcatggc tggtccaaat gcaaatgcaa atggtaatgc tggacgaaca    1980
aacatggaga ttgctaatga ggtcatcgac aaaagtggac atgcaggagg tggcaatggg    2040
agtggcagtg gcagtggcaa tgacacatat gtcaaacggc ttgcagcggg cttgacacca    2100
cgacaagcac aactaaagaa atatagagag aaaaagaaag atcgaaactt tgggaaaaag    2160
gtagcctgtt ttcaattgca tgtttgtggt                                    2190
```

<210> SEQ ID NO 3
<211> LENGTH: 730
<212> TYPE: PRT
<213> ORGANISM: Sorghum bicolor
<220> FEATURE:
<221> NAME/KEY: UNSURE
<222> LOCATION: (723)..(723)
<223> OTHER INFORMATION: Xaa is any natural amino acid

<400> SEQUENCE: 3

```
Cys Ser Gln Gln Leu Ala Thr Val Asp Gly Pro Ser Leu Arg Asp Ala
1               5                   10                  15

Thr Arg Met Met Leu Arg Asn Asn Asn Asn Leu Arg Ser Asn Gly
            20                  25                  30

Pro Ser Asp Gly Leu Leu Ser Arg Pro Thr Pro Ala Val Leu Gln Asp
        35                  40                  45

Asp Asp Asp Gly Gly Asp Asp Thr Glu Asn Gln Gln Gln Glu Ala
    50                  55                  60

Val Tyr Trp Glu Arg Phe Leu Gln Lys Lys Thr Ile Asn Val Leu Leu
65                  70                  75                  80

Val Glu Ser Asp Asp Cys Thr Arg Arg Val Val Ser Ala Leu Leu Arg
                85                  90                  95

His Cys Met Tyr Gln Val Ile Ser Ala Glu Asn Gly Gln Gln Ala Trp
            100                 105                 110

Asn Tyr Leu Glu Asp Lys Gln Asn Asn Ile Asp Ile Val Leu Ile Glu
        115                 120                 125

Val Phe Met Pro Gly Val Ser Gly Ile Ser Leu Leu Ser Arg Ile Met
    130                 135                 140

Ser His Asn Ile Cys Lys Asn Ile Pro Val Ile Met Met Ser Ser Asn
145                 150                 155                 160

Asp Ala Arg Asn Thr Val Phe Lys Cys Leu Ser Lys Gly Ala Val Asp
                165                 170                 175
```

```
Phe Leu Val Lys Pro Ile Arg Lys Asn Glu Leu Lys Asn Leu Trp Gln
            180                 185                 190

His Val Trp Arg Arg Cys His Ser Ser Gly Ser Gly Ser Glu Ser
            195                 200                 205

Gly Ile Gln Thr Gln Lys Cys Gly Lys Ser Lys Gly Lys Glu Ser
            210                 215                 220

Gly Asn Asn Ser Gly Ser Asn Asp Ser His Asp Asn Glu Ala Asp Met
225                 230                 235                 240

Gly Leu Asn Ala Arg Asp Asp Ser Asp Asn Gly Ser Gly Thr Gln Ala
                245                 250                 255

Gln Ser Ser Trp Thr Lys Cys Ala Val Glu Met Asp Ser Pro Gln Ala
            260                 265                 270

Met Ser Leu Asp His Leu Ala Asp Ser Pro Asp Ser Thr Cys Ala Gln
            275                 280                 285

Val Ile His Pro Lys Ser Glu Ile Cys Ser Asn Arg Arg Leu Pro Asp
            290                 295                 300

Asp Phe Lys Glu Lys Asp Leu Glu Ile Gly Gly Pro Gly Asn Leu Tyr
305                 310                 315                 320

Ile Asp His Gln Ser Ser Pro Asn Glu Arg Pro Ile Lys Ala Thr Asp
                325                 330                 335

Gly Arg Cys Glu Tyr Pro Pro Lys Asn Asn Ser Lys Glu Ser Met Met
            340                 345                 350

Gln Asn Leu Glu Asp Pro Thr Val Arg Ala Ala Asp Leu Ile Gly Ser
            355                 360                 365

Met Ala Lys Asn Met Asp Thr Gln Glu Ala Ala Arg Ala Ala Asp Thr
            370                 375                 380

Pro Asn Leu Pro Ser Lys Val Pro Glu Gly Lys Asp Lys Asn Lys His
385                 390                 395                 400

Asp Lys Ile Leu Pro Ser Leu Glu Leu Ser Leu Lys Arg Ser Arg Ser
                405                 410                 415

Cys Gly Asp Gly Ala Asn Thr Val Lys Ala Asp Glu Gln Gln Asn Val
            420                 425                 430

Leu Arg Gln Ser Asn Leu Ser Ala Phe Thr Arg Tyr His Thr Ser Thr
            435                 440                 445

Ala Ser Asn Gln Gly Gly Thr Gly Leu Val Gly Ser Cys Ser Pro His
            450                 455                 460

Asp Asn Ser Ser Glu Ala Met Lys Thr Asp Ser Thr Tyr Asn Met Lys
465                 470                 475                 480

Ser Asn Ser Asp Ala Ala Pro Ile Lys Gln Gly Ser Asn Gly Ser Ser
                485                 490                 495

Asn Asn Asn Asp Met Gly Ser Thr Thr Lys Asn Val Val Thr Lys Pro
            500                 505                 510

Thr Thr Asn Asn Lys Asp Arg Val Met Leu Pro Ser Ser Ala Ile Asn
            515                 520                 525

Lys Ala Asn Gly His Thr Ser Ala Phe His Pro Val Gln His Trp Thr
            530                 535                 540

Met Val Pro Ala Asn Ala Ala Gly Gly Thr Ala Lys Ala Asp Glu Val
545                 550                 555                 560

Ala Asn Ile Ala Gly Tyr Pro Ser Gly Asp Met Gln Cys Asn Leu Met
                565                 570                 575

Gln Trp Tyr Pro Arg Pro Thr Leu His Tyr Val Gln Phe Asp Gly Ala
            580                 585                 590

Arg Glu Asn Gly Gly Ser Gly Ala Leu Gln Cys Gly Ser Ser Asn Val
```

```
              595                 600                 605
Phe Asp Pro Val Glu Gly Gln Ala Thr Asn Tyr Gly Val Asn Arg
610                 615                 620

Ser Asn Ser Gly Ser Asn Asn Ala Thr Lys Gly Gln Asn Gly Ser Asn
625                 630                 635                 640

Thr Val Gly Ala Ser Met Ala Gly Pro Asn Ala Asn Ala Asn Gly Asn
                645                 650                 655

Ala Gly Arg Thr Asn Met Glu Ile Ala Asn Glu Val Ile Asp Lys Ser
                660                 665                 670

Gly His Ala Gly Gly Gly Asn Gly Ser Gly Ser Gly Gly Asn Asp
                675                 680                 685

Thr Tyr Val Lys Arg Leu Ala Ala Gly Leu Thr Pro Arg Gln Ala Gln
690                 695                 700

Leu Lys Lys Tyr Arg Glu Lys Lys Lys Asp Arg Asn Phe Gly Lys Lys
705                 710                 715                 720

Val Ala Xaa Phe Ser Ile Ala Cys Leu Trp
                725                 730

<210> SEQ ID NO 4
<211> LENGTH: 730
<212> TYPE: PRT
<213> ORGANISM: Sorghum bicolor
<220> FEATURE:
<221> NAME/KEY: UNSURE
<222> LOCATION: (723)..(723)
<223> OTHER INFORMATION: Xaa is any natural amino acid

<400> SEQUENCE: 4

Cys Ser Gln Gln Leu Ala Thr Val Asp Gly Pro Ser Leu Arg Asp Ala
1               5                   10                  15

Thr Arg Met Met Leu Arg Asn Asn Asn Asn Leu Arg Ser Asn Gly
                20                  25                  30

Pro Ser Asp Gly Leu Leu Ser Arg Pro Thr Pro Ala Val Leu Gln Asp
            35                  40                  45

Asp Asp Asp Gly Gly Asp Asp Thr Glu Asn Gln Gln Gln Glu Ala
50                  55                  60

Val Tyr Trp Glu Arg Phe Leu Gln Lys Lys Thr Ile Asn Val Leu Leu
65                  70                  75                  80

Val Glu Ser Asp Asp Cys Thr Arg Arg Val Ser Ala Leu Leu Arg
                85                  90                  95

His Cys Met Tyr Gln Val Ile Ser Ala Glu Asn Gly Gln Gln Ala Trp
                100                 105                 110

Asn Tyr Leu Glu Asp Lys Gln Asn Asn Ile Asp Ile Val Leu Ile Glu
            115                 120                 125

Val Phe Met Pro Gly Val Ser Gly Ile Ser Leu Leu Ser Arg Ile Met
130                 135                 140

Ser His Asn Ile Cys Lys Asn Ile Pro Val Ile Met Met Ser Ser Asn
145                 150                 155                 160

Asp Ala Arg Asn Thr Val Phe Lys Cys Leu Ser Lys Gly Ala Val Asp
                165                 170                 175

Phe Leu Val Asn Pro Ile Arg Lys Asn Glu Leu Lys Asn Leu Trp Gln
            180                 185                 190

His Val Trp Arg Arg Cys His Ser Ser Gly Ser Gly Ser Glu Ser
        195                 200                 205

Gly Ile Gln Thr Gln Lys Cys Gly Lys Ser Lys Gly Gly Lys Glu Ser
210                 215                 220
```

```
Gly Asn Asn Ser Gly Ser Asn Asp Ser His Asp Asn Glu Ala Asp Met
225                 230                 235                 240

Gly Leu Asn Ala Arg Asp Ser Asp Asn Gly Ser Gly Thr Gln Ala
            245                 250                 255

Gln Ser Ser Trp Thr Lys Cys Ala Val Glu Met Asp Ser Pro Gln Ala
        260                 265                 270

Met Ser Leu Asp Gln Leu Ala Asp Ser Pro Asp Ser Thr Cys Ala Gln
        275                 280                 285

Val Ile His Pro Lys Ser Glu Ile Cys Ser Asn Arg Arg Leu Pro Asp
        290                 295                 300

Asp Phe Lys Glu Lys Asp Leu Glu Ile Gly Pro Gly Asn Leu Tyr
305                 310                 315                 320

Ile Asp His Gln Ser Ser Pro Asn Glu Arg Pro Ile Lys Ala Thr Asp
                325                 330                 335

Gly Arg Cys Glu Tyr Pro Pro Lys Asn Asn Ser Lys Glu Ser Met Met
            340                 345                 350

Gln Asn Leu Glu Asp Pro Thr Val Arg Ala Ala Asp Leu Ile Gly Ser
        355                 360                 365

Met Ala Lys Asn Met Asp Thr Gln Glu Ala Ala Arg Ala Ala Asp Thr
370                 375                 380

Pro Asn Leu Pro Ser Lys Val Pro Glu Gly Lys Asp Lys Asn Lys His
385                 390                 395                 400

Asp Lys Ile Leu Pro Ser Leu Glu Leu Ser Leu Lys Arg Ser Arg Ser
            405                 410                 415

Cys Gly Tyr Gly Ala Asn Thr Val Lys Ala Asp Glu Gln Gln Asn Val
            420                 425                 430

Leu Arg Gln Ser Asn Leu Ser Ala Phe Thr Arg Tyr His Thr Ser Thr
        435                 440                 445

Ala Ser Asn Gln Gly Gly Thr Gly Leu Val Gly Ser Cys Ser Pro His
        450                 455                 460

Asp Asn Ser Ser Glu Ala Met Lys Thr Asp Ser Thr Tyr Asn Met Lys
465                 470                 475                 480

Ser Asn Ser Asp Ala Ala Pro Ile Lys Gln Gly Ser Asn Gly Ser Ser
                485                 490                 495

Asn Asn Asn Asp Met Gly Ser Thr Thr Lys Asn Val Val Thr Lys Pro
            500                 505                 510

Thr Thr Asn Asn Lys Asp Arg Val Met Leu Pro Ser Ser Ala Ile Asn
        515                 520                 525

Lys Ala Asn Gly His Thr Ser Ala Phe His Pro Val Gln His Trp Thr
        530                 535                 540

Met Val Pro Ala Asn Ala Ala Gly Gly Thr Ala Lys Ala Asp Glu Val
545                 550                 555                 560

Ala Asn Ile Ala Gly Tyr Pro Ser Gly Asp Met Gln Cys Asn Leu Met
                565                 570                 575

Gln Trp Tyr Pro Arg Pro Thr Leu His Tyr Val Gln Phe Asp Gly Ala
        580                 585                 590

Arg Glu Asn Gly Gly Ser Gly Ala Leu Glu Cys Gly Ser Ser Asn Val
        595                 600                 605

Phe Asp Pro Pro Val Glu Gly Gln Ala Thr Asn Tyr Gly Val Asn Arg
610                 615                 620

Ser Asn Ser Gly Ser Asn Asn Ala Thr Lys Gly Gln Asn Gly Ser Asn
625                 630                 635                 640

Thr Val Gly Ala Ser Met Ala Gly Pro Asn Ala Asn Ala Asn Gly Asn
            645                 650                 655
```

```
Ala Gly Arg Thr Asn Met Glu Ile Ala Asn Glu Val Ile Asp Lys Ser
            660                 665                 670

Gly His Ala Gly Gly Asn Gly Ser Gly Ser Gly Asn Asp
            675                 680             685

Thr Tyr Val Lys Arg Leu Ala Ala Gly Leu Thr Pro Arg Gln Ala Gln
        690                 695                 700

Leu Lys Lys Tyr Arg Glu Lys Lys Asp Arg Asn Phe Gly Lys Lys
705                 710                 715                 720

Val Ala Xaa Phe Ser Ile Ala Cys Leu Trp
            725                 730

<210> SEQ ID NO 5
<211> LENGTH: 742
<212> TYPE: PRT
<213> ORGANISM: Oryza sativa

<400> SEQUENCE: 5

Met Met Gly Thr Ala His His Asn Gln Thr Ala Gly Ser Ala Leu Gly
1               5                   10                  15

Val Gly Val Gly Asp Ala Asn Asp Ala Val Pro Gly Ala Gly Gly Gly
            20                  25                  30

Gly Tyr Ser Asp Pro Asp Gly Gly Pro Ile Ser Gly Val Gln Arg Pro
        35                  40                  45

Pro Gln Val Cys Trp Glu Arg Phe Ile Gln Lys Lys Thr Ile Lys Val
    50                  55                  60

Leu Leu Val Asp Ser Asp Asp Ser Thr Arg Gln Val Val Ser Ala Leu
65                  70                  75                  80

Leu Arg His Cys Met Tyr Glu Val Ile Pro Ala Glu Asn Gly Gln Gln
                85                  90                  95

Ala Trp Thr Tyr Leu Glu Asp Met Gln Asn Ser Ile Asp Leu Val Leu
            100                 105                 110

Thr Glu Val Val Met Pro Gly Val Ser Gly Ile Ser Leu Leu Ser Arg
        115                 120                 125

Ile Met Asn His Asn Ile Cys Lys Asn Ile Pro Val Ile Met Met Ser
    130                 135                 140

Ser Asn Asp Ala Met Gly Thr Val Phe Lys Cys Leu Ser Lys Gly Ala
145                 150                 155                 160

Val Asp Phe Leu Val Lys Pro Ile Arg Lys Asn Glu Leu Lys Asn Leu
                165                 170                 175

Trp Gln His Val Trp Arg Arg Cys His Ser Ser Gly Ser Gly Ser
            180                 185                 190

Glu Ser Gly Ile Gln Thr Gln Lys Cys Ala Lys Ser Lys Ser Gly Asp
        195                 200                 205

Glu Ser Asn Asn Asn Gly Ser Asn Asp Asp Asp Asp Gly
    210                 215                 220

Val Ile Met Gly Leu Asn Ala Arg Asp Gly Ser Asp Asn Gly Ser Gly
225                 230                 235                 240

Thr Gln Ala Gln Ser Ser Trp Thr Lys Arg Ala Val Glu Ile Asp Ser
                245                 250                 255

Pro Gln Ala Met Ser Pro Asp Gln Leu Ala Asp Pro Asp Ser Thr
            260                 265                 270

Cys Ala Gln Val Ile His Leu Lys Ser Asp Ile Cys Ser Asn Arg Trp
        275                 280                 285

Leu Pro Cys Thr Ser Asn Lys Asn Ser Lys Lys Gln Lys Glu Thr Asn
    290                 295                 300
```

```
Asp Asp Phe Lys Gly Lys Asp Leu Glu Ile Gly Ser Pro Arg Asn Leu
305                 310                 315                 320

Asn Thr Ala Tyr Gln Ser Ser Pro Asn Glu Arg Ser Ile Lys Pro Thr
                325                 330                 335

Asp Arg Arg Asn Glu Tyr Pro Leu Gln Asn Asn Ser Lys Glu Ala Ala
            340                 345                 350

Met Glu Asn Leu Glu Glu Ser Ser Val Arg Ala Ala Asp Leu Ile Gly
        355                 360                 365

Ser Met Ala Lys Asn Met Asp Ala Gln Gln Ala Ala Arg Ala Ala Asn
    370                 375                 380

Ala Pro Asn Cys Ser Ser Lys Val Pro Glu Gly Lys Asp Lys Asn Arg
385                 390                 395                 400

Asp Asn Ile Met Pro Ser Leu Glu Leu Ser Leu Lys Arg Ser Arg Ser
                405                 410                 415

Thr Gly Asp Gly Ala Asn Ala Ile Gln Glu Glu Gln Arg Asn Val Leu
            420                 425                 430

Arg Arg Ser Asp Leu Ser Ala Phe Thr Arg Tyr His Thr Pro Val Ala
        435                 440                 445

Ser Asn Gln Gly Gly Thr Gly Phe Met Gly Ser Cys Ser Leu His Asp
    450                 455                 460

Asn Ser Ser Glu Ala Met Lys Thr Asp Ser Ala Tyr Asn Met Lys Ser
465                 470                 475                 480

Asn Ser Asp Ala Ala Pro Ile Lys Gln Gly Ser Asn Gly Ser Ser Asn
                485                 490                 495

Asn Asn Asp Met Gly Ser Thr Thr Lys Asn Val Val Thr Lys Pro Ser
            500                 505                 510

Thr Asn Lys Glu Arg Val Met Ser Pro Ser Ala Val Lys Ala Asn Gly
        515                 520                 525

His Thr Ser Ala Phe His Pro Ala Gln His Trp Thr Ser Pro Ala Asn
    530                 535                 540

Thr Thr Gly Lys Glu Lys Thr Asp Glu Val Ala Asn Asn Ala Ala Lys
545                 550                 555                 560

Arg Ala Gln Pro Gly Glu Val Gln Ser Asn Leu Val Gln His Pro Arg
                565                 570                 575

Pro Ile Leu His Tyr Val His Phe Asp Val Ser Arg Glu Asn Gly Gly
            580                 585                 590

Ser Gly Ala Pro Gln Cys Gly Ser Ser Asn Val Phe Asp Pro Pro Val
        595                 600                 605

Glu Gly His Ala Ala Asn Tyr Gly Val Asn Gly Ser Asn Ser Gly Ser
    610                 615                 620

Asn Asn Gly Ser Asn Gly Gln Asn Gly Ser Thr Thr Ala Val Asp Ala
625                 630                 635                 640

Glu Arg Pro Asn Met Glu Ile Ala Asn Gly Thr Ile Asn Lys Ser Gly
                645                 650                 655

Pro Gly Gly Gly Asn Gly Ser Gly Ser Gly Ser Gly Asn Asp Met Tyr
            660                 665                 670

Leu Lys Arg Phe Thr Gln Arg Glu His Arg Val Ala Ala Val Ile Lys
        675                 680                 685

Phe Arg Gln Lys Arg Lys Glu Arg Asn Phe Gly Lys Lys Val Arg Tyr
    690                 695                 700

Gln Ser Arg Lys Arg Leu Ala Glu Gln Arg Pro Arg Val Arg Gly Gln
705                 710                 715                 720

Phe Val Arg Gln Ala Val Gln Asp Gln Gln Gln Gln Gly Gly Gly Arg
```

```
                725                 730                 735
Glu Ala Ala Ala Asp Arg
        740

<210> SEQ ID NO 6
<211> LENGTH: 565
<212> TYPE: DNA
<213> ORGANISM: Sorghum bicolor

<400> SEQUENCE: 6
agccgccacg tacgtgcttg cttgctagct gctacagaag tgctggcggt ggcgatgtat    60
atatatgcca taatgccgag ccaatttcac ctcctatttt agagtattta tttatttaat   120
tacctattat tgcccaggga gcgagtgtgg ttggaaatta attggctgca tccctacatt   180
tttacattac ttgcacaggt actgctgcct agttagctat gaaacatgca ttggcttcat   240
tattctgctc taacggtacg aatggattcc tggtttctta aggttgcttg ctcttttgc    300 cttttcgcag gccaggccac caccaacctc cacttcctcc atccatccat ccatttgctg   360
ctgattcacc acctagtagc agcagcagca gctacacaga cacaggtatt tcttccccgg   420
ccggccggcg tctctctact ctcctgcctc ccattcattc ttcagagagc acgattatta   480
attttccaga gggcatgatt taatgtcaat atctcaaaat gatgctaccc tctttctccc   540
agagggccag agatatgatc cttta                                         565

<210> SEQ ID NO 7
<211> LENGTH: 567
<212> TYPE: DNA
<213> ORGANISM: Sorghum bicolor

<400> SEQUENCE: 7
agccgccacg tacgtgcttg cttgctagct gctacagaag tgctggcggt ggcgatgtat    60
atatatgcca taatgccgag ccaatttcac ctcctatttt agaatattta tttatttatt   120
tacttattat attgcccacg gaacgagtgt ggttggaaat taaattggct gcatcctaca   180
tttttacatt acatgcacat acggcacagg caggtactgc tgcctagtta gctatgaaac   240
atgcattggc ttcattattc tgctctaacg gtacaaatgg attcctggtt tcttaagctt   300
gcttgctctt tttgcctttt cgcaggccag gcaaccacca acctccactt cctccatcca   360
tccatttgct gctgattcac cacctagcag cagctacaca gacaggtatt tcttccccgg   420
ccggccggcg tctctctact ctcctgcctc ccattcattc ttcagagagg cacaattat    480 taattttcca gagggcatga tttaatgtca atatctcaaa atgatgctac cctctttctc   540
ccagagggac agagatttga cctttta                                       567

<210> SEQ ID NO 8
<211> LENGTH: 220
<212> TYPE: DNA
<213> ORGANISM: Sorghum bicolor

<400> SEQUENCE: 8
ttgttttatc ttcctaccta gctatatata gcgattcgtt ttgtcattca ctttgcagca    60
atcacacaga cgaggtgccc ttgaaggcga acaaggagta atatgcgccc cagtgtctat   120
tcactaacca acgacttgcc tcgaatcaat cccaccactt tcgtctacct cttcgagtca   180
ggctgagata tgcgaggtgt ctgtagtcag caactggcca                         220

<210> SEQ ID NO 9
<211> LENGTH: 220
```

```
<212> TYPE: DNA
<213> ORGANISM: Sorghum bicolor

<400> SEQUENCE: 9
ttgttttatc ttcctaccta gctatatata gctattcgtt ttgtcattca ctttgcagca      60
atcacactga cgaggtgccc ttgaaggcaa acaaggagta atatgcgccc cagtgtctat     120
tcactaacca acgacttgcc tcgaatcaat cccaccactt tcgtctacct cttcgagtca     180
ggctgagata tgcgaggtgt ctgtagtcag caactggcca                           220
```